(12) United States Patent
Pouliquen et al.

(10) Patent No.: US 8,084,045 B2
(45) Date of Patent: *Dec. 27, 2011

(54) PHARMACEUTICAL FORMULATIONS FOR THE PROLONGED RELEASE OF ACTIVE PRINCIPLE(S) AND THEIR APPLICATIONS

(75) Inventors: Gauthier Pouliquen, Lyons (FR); Olivier Soula, Meyzieu (FR); Rémi Meyrueix, Lyons (FR); Florence Nicolas, Manissieux (FR)

(73) Assignee: Flamel Technologies (FR)

( * ) Notice: Subject to any disclaimer, the term of this patent is extended or adjusted under 35 U.S.C. 154(b) by 865 days.

This patent is subject to a terminal disclaimer.

(21) Appl. No.: 10/580,023

(22) PCT Filed: Nov. 19, 2004

(86) PCT No.: PCT/FR2004/050603
§ 371 (c)(1),
(2), (4) Date: Mar. 27, 2007

(87) PCT Pub. No.: WO2005/051416
PCT Pub. Date: Jun. 9, 2005

(65) Prior Publication Data
US 2007/0196497 A1    Aug. 23, 2007

(30) Foreign Application Priority Data
Nov. 21, 2003    (FR) ..................... 03 50887

(51) Int. Cl.
- *A61K 9/32* (2006.01)
- *A61K 9/52* (2006.01)
- *A61K 9/54* (2006.01)
- *A61K 9/64* (2006.01)
- *A61K 38/00* (2006.01)

(52) U.S. Cl. ..................... 424/280.1; 424/457; 424/460; 424/462; 514/1.1

(58) Field of Classification Search .................... None
See application file for complete search history.

(56) References Cited

U.S. PATENT DOCUMENTS

| | | |
|---|---|---|
| 2,680,749 A | 6/1954 | Cawley et al. |
| 3,536,672 A | 10/1970 | Fujimoto et al. |
| 4,126,628 A | 11/1978 | Paquet |
| 4,321,253 A | 3/1982 | Beatty |
| 4,351,337 A | 9/1982 | Sidman |
| 4,443,549 A | 4/1984 | Sadowski |
| 4,450,150 A | 5/1984 | Sidman |
| 4,615,697 A | 10/1986 | Robinson |
| 4,652,441 A | 3/1987 | Okada et al. |
| 4,661,345 A | 4/1987 | Tuomanen |
| 4,748,023 A | 5/1988 | Tamas et al. |
| 4,766,106 A | 8/1988 | Katre et al. |
| 4,835,293 A | 5/1989 | Bhatia |
| 4,888,398 A | 12/1989 | Bichon et al. |
| 4,892,733 A | 1/1990 | Bichon et al. |
| 4,894,240 A | 1/1990 | Geoghegan et al. |
| 4,904,479 A | 2/1990 | Illum |
| 4,976,968 A | 12/1990 | Steiner |
| 5,023,349 A | 6/1991 | Bhatia |
| 5,084,278 A | 1/1992 | Mehta |
| 5,102,872 A | 4/1992 | Singh et al. |
| 5,204,108 A | 4/1993 | Illum |
| 5,286,495 A | 2/1994 | Batich et al. |
| 5,286,497 A | 2/1994 | Hendrickson et al. |
| 5,399,331 A | 3/1995 | Loughrey et al. |
| 5,449,513 A | 9/1995 | Yokoyama et al. |
| 5,510,103 A | 4/1996 | Yokoyama et al. |
| 5,514,380 A | 5/1996 | Song et al. |
| 5,589,455 A | 12/1996 | Woo |
| 5,609,872 A | 3/1997 | Ahlborg et al. |
| 5,656,722 A | 8/1997 | Dorschug |
| 5,780,579 A | 7/1998 | Soula et al. |
| 5,834,422 A | 11/1998 | Balschmidt |
| 5,852,109 A | 12/1998 | Makino et al. |
| 5,863,900 A | 1/1999 | Russell-Jones |
| 5,869,703 A | 2/1999 | Kim et al. |
| 5,872,210 A | 2/1999 | Medabalimi |

(Continued)

FOREIGN PATENT DOCUMENTS

CA    2068366    11/1992

(Continued)

OTHER PUBLICATIONS

Forssen et al., *Cancer Res.* 43: 546 (1983).

(Continued)

*Primary Examiner* — Cecilia J Tsang
*Assistant Examiner* — Satyanarayana Gudibande
(74) *Attorney, Agent, or Firm* — Patton Boggs LLP

(57) ABSTRACT

The present invention relates to novel pharmaceutical formulations based on stable, fluid aqueous colloidal suspensions for the prolonged release of active principle(s), particularly protein active principle(s), and to the applications, especially therapeutic applications, of these formulations.

The object of the invention is to propose a fluid pharmaceutical formulation for the prolonged release of active principle (s) that makes it possible, after parenteral injection, to increase significantly the in vivo release time of a therapeutic protein while at the same time reducing the plasma concentration peak of the active protein, said formulation furthermore being stable on storage and also being biocompatible, biodegradable, non-toxic and non-immunogenic and having a good local tolerance.

The formulation according to the invention is an aqueous colloidal suspension of low viscosity based on submicronic particles of water-soluble biodegradable polymer PO carrying hydrophobic groups (HG), said particles being non-covalently associated with at least one active principle (AP) and forming a gelled deposit at the injection site, this gelling being caused by a protein present in the physiological medium.

24 Claims, 2 Drawing Sheets

U.S. PATENT DOCUMENTS

| | | | |
|---|---|---|---|
| 5,876,969 | A | 3/1999 | Fleer et al. |
| 5,904,936 | A | 5/1999 | Huille et al. |
| 5,939,485 | A | 8/1999 | Bromberg et al. |
| 5,981,761 | A | 11/1999 | Chou et al. |
| 6,143,314 | A | 11/2000 | Chandrashekar et al. |
| 6,153,193 | A | 11/2000 | Kabanov et al. |
| 6,180,141 | B1 | 1/2001 | Lemercier et al. |
| 6,193,953 | B1 | 2/2001 | Lohrmann et al. |
| 6,197,535 | B1 | 3/2001 | Bandyopadhyay et al. |
| 6,201,072 | B1 | 3/2001 | Rathi et al. |
| 6,235,282 | B1 | 5/2001 | Riviere et al. |
| 6,284,267 | B1 | 9/2001 | Aneja |
| 6,309,663 | B1 | 10/2001 | Patel et al. |
| 6,313,095 | B1 | 11/2001 | Adams et al. |
| 6,313,260 | B2 | 11/2001 | Gruning et al. |
| 6,320,017 | B1 | 11/2001 | Ansell |
| 6,500,448 | B1 | 12/2002 | Johnson et al. |
| 6,576,254 | B1 | 6/2003 | Uchegbu |
| 6,607,714 | B1 | 8/2003 | Dupuis et al. |
| 6,630,171 | B1 * | 10/2003 | Huille et al. ............. 424/489 |
| 6,933,269 | B2 | 8/2005 | Jordan et al. |
| 6,946,146 | B2 | 9/2005 | Mulye |
| 7,030,155 | B2 * | 4/2006 | Lambert et al. ............ 514/449 |
| 7,226,618 | B1 | 6/2007 | Touraud et al. |
| 7,250,436 | B2 | 7/2007 | Ducray et al. |
| 7,261,875 | B2 | 8/2007 | Li et al. |
| 7,270,832 | B2 | 9/2007 | Bryson et al. |
| 7,311,901 | B2 | 12/2007 | Seo et al. |
| 7,659,365 | B2 | 2/2010 | Soula et al. |
| 7,678,882 | B2 | 3/2010 | Angot et al. |
| 7,683,024 | B2 * | 3/2010 | Chan et al. ............... 514/2 |
| 7,709,445 | B2 | 5/2010 | Soula et al. |
| 2001/0000510 | A1 | 4/2001 | Sakurai et al. |
| 2002/0068085 | A1 | 6/2002 | Rudnic et al. |
| 2003/0133980 | A1 | 7/2003 | Costantino et al. |
| 2004/0038885 | A1 | 2/2004 | Bryson et al. |
| 2004/0063628 | A1 | 4/2004 | Piccariello et al. |
| 2004/0071716 | A1 | 4/2004 | Jansen et al. |
| 2004/0175424 | A1 | 9/2004 | Castan et al. |
| 2005/0158392 | A1 | 7/2005 | Kim et al. |
| 2006/0099264 | A1 * | 5/2006 | Chan et al. ............... 424/486 |
| 2007/0010652 | A1 | 1/2007 | Angot et al. |
| 2007/0160568 | A1 | 7/2007 | Angot et al. |
| 2007/0178126 | A1 | 8/2007 | Angot et al. |
| 2007/0190162 | A1 | 8/2007 | Caillol et al. |
| 2007/0196497 | A1 | 8/2007 | Pouliquen et al. |
| 2007/0218142 | A1 | 9/2007 | Bignon et al. |
| 2007/0248686 | A1 | 10/2007 | Touraud et al. |
| 2007/0254828 | A1 | 11/2007 | Dubreucq et al. |
| 2007/0265192 | A1 | 11/2007 | Soula et al. |
| 2007/0269517 | A1 | 11/2007 | Pouliquen et al. |
| 2008/0014250 | A1 | 1/2008 | Soula et al. |
| 2008/0015332 | A1 | 1/2008 | Bryson et al. |
| 2008/0026070 | A1 | 1/2008 | Bonnet-Gonnet |
| 2008/0102128 | A1 | 5/2008 | Constancis |
| 2009/0012028 | A1 | 1/2009 | Chan et al. |
| 2009/0110742 | A1 | 4/2009 | Constancis et al. |
| 2010/0048735 | A1 | 2/2010 | Chan et al. |

FOREIGN PATENT DOCUMENTS

| | | |
|---|---|---|
| CN | 1183040 | 5/1998 |
| CN | 1282345 | 1/2001 |
| EP | 0 198 769 | 10/1986 |
| EP | 0 179 023 | 1/1991 |
| EP | 0 583 955 | 2/1994 |
| EP | 0 601 508 | 6/1994 |
| EP | 0 721 776 | 7/1996 |
| EP | 0 734 720 | 10/1996 |
| EP | 0 963 758 | 12/1999 |
| FR | 2 313 915 | 1/1977 |
| FR | 2 533 209 | 3/1984 |
| FR | 2 670 112 | 6/1992 |
| FR | 2 692 263 | 12/1993 |
| FR | 2732218 | 10/1996 |
| FR | 2 746 035 | 9/1997 |
| FR | 2786098 | 5/2000 |
| FR | 2801226 | 5/2001 |
| FR | 2822834 | 10/2002 |
| FR | 0350641 | 10/2003 |
| FR | 2838964 | 10/2003 |
| FR | 2 840 614 | 12/2003 |
| FR | 0207008 | 12/2003 |
| FR | 2 843 117 | 2/2004 |
| FR | 0209670 | 2/2004 |
| FR | 2 855 521 | 12/2004 |
| FR | 0350190 | 12/2004 |
| FR | 2 860 516 | 4/2005 |
| FR | 2 873 040 | 1/2006 |
| FR | 2 881 140 | 7/2006 |
| FR | 2 915 748 | 11/2008 |
| GB | 966 760 | 8/1964 |
| GB | 1 024 393 | 3/1966 |
| GB | 1 202 765 | 8/1970 |
| GB | 2 041 517 | 9/1980 |
| GB | 2 240 547 | 8/1991 |
| JP | 2002-194078 | 7/2002 |
| JP | 2002-194080 | 7/2002 |
| JP | 2003-327693 | 11/2003 |
| WO | WO 85/02092 | 5/1985 |
| WO | WO 87/02219 | 4/1987 |
| WO | WO 87/03891 | 7/1987 |
| WO | WO 88/01213 | 2/1988 |
| WO | WO 88/07078 | 9/1988 |
| WO | WO 89/08449 | 9/1989 |
| WO | WO 91/06286 | 5/1991 |
| WO | WO 91/06287 | 5/1991 |
| WO | WO 96/29991 | 10/1996 |
| WO | WO 96/40279 | 12/1996 |
| WO | WO 97/02810 | 1/1997 |
| WO | WO 97/34584 | 9/1997 |
| WO | WO-9811874 | 3/1998 |
| WO | WO-9918142 | 4/1999 |
| WO | WO 99/61512 | 12/1999 |
| WO | WO-0018821 | 4/2000 |
| WO | WO-0030618 | 6/2000 |
| WO | WO 00/71163 | 11/2000 |
| WO | WO 00/78791 | 12/2000 |
| WO | WO 01/37809 | 5/2001 |
| WO | WO 02/28521 | 4/2002 |
| WO | WO 02/39984 | 5/2002 |
| WO | WO 02/078677 | 10/2002 |
| WO | WO 02/098951 | 12/2002 |
| WO | WO 02/098952 | 12/2002 |
| WO | WO 03/002096 | 1/2003 |
| WO | WO 03/013467 | 2/2003 |
| WO | WO 03/090727 | 11/2003 |
| WO | WO 03/010403 | * 12/2003 |
| WO | WO 03/104202 | 12/2003 |
| WO | WO 03/104303 | 12/2003 |
| WO | WO 2004/013206 | 2/2004 |
| WO | WO 2004/060968 | 7/2004 |
| WO | WO 2004/108796 | 12/2004 |
| WO | WO 2005/033181 | 4/2005 |
| WO | WO 2005/051416 | 6/2005 |
| WO | WO 2005/051417 | 6/2005 |
| WO | WO 2005/051418 | 6/2005 |
| WO | WO 2006/016078 | 2/2006 |
| WO | WO 2007/034320 | 3/2007 |
| WO | WO 2007/116143 | 10/2007 |

OTHER PUBLICATIONS

Regalado, J. et al., *Macromolecules* 32: 8580 (1999).
Fuller et al., *Biopolymers* 15: 1869 (1976).
Kricheldorf, H.R., Alpha-Amino Acid N-Carboxy Anhydrides and Related Heterocycles Springer Verlag (1987).
Tomida et al., *Polymer* 38: 4733-36 (1997).
Gupta, P.K. et al., *Injectable Drug Development* Interpharm Press, Denver, Colorado (1999).
Gao J.Y., et al., *Anal. Chem.* 69: 2945 (1997).
Dekker, M., *Surfactant Science Series* vol. 22, Surfactant Solutions, Ed. R. Zana, Chap. 3 (1984).
In the U.S. Patent and Trademark Office, Non-Final Office Action in re: U.S. Appl. No. 10/580,035, dated Dec. 3, 2008, 24 pages.
In the U.S. Patent and Trademark Office Final Office Action in re: U.S. Appl. No. 10/580,035, dated Aug. 7, 2009, 16 pages.

In the U.S. Patent and Trademark Office Non-Final Office Action in re: U.S. Appl. No. 10/580,037, dated Feb. 18, 2010, 15 pages.
In the U.S. Patent and Trademark Office Non-Final Office Action in re: U.S. Appl. No. 10/580,035, dated Jul. 6, 2010, 13 pages.
In the U.S. Patent and Trademark Office Non-Final Office Action in re: U.S. Appl. No. 10/580,037, dated Aug. 17, 2010, 19 pages.
Akiyoshi et al., "Microscopic Structure and Thermoresponsiveness of a Hydrogel Nanoparticle by Self-Assembly of a Hydrophobized Polysaccharide," *Macromolecules*, 1997; 30:857-861.
Conover et al., "Camptothecin Delivery Systems: The Utility of Amino Acid Spacers for the Conjugation of Camptothecin with Poyethylene Glycol to Create Prodrugs," *Anti-Cancer Drug Design*, 1999; 14:499-506.
Edwards et al., "The Effect of an Intralesional Sustained-Release Formulationof Interferon Alfa-2b on Basal Cell Carcinomas," *Arch. Dermatol.*, 1990; 126:1029-1032.
Eliaz et al., "Characterization of a Polymeric PLGA-Injectable Implant Delivery System for the Controlled Release of Proteins," *J. Biomed Mater. Res.*, 2000; 50:388-396.
Hora et al., "Controlled Release of Interleukin-2 from Biodegradable Microspheres," *Biotechnology*, 1990; 8(8):755-758.
In the U.S. Patent and Trademark Office, Non-Final Office Action in re: U.S. Appl. No. 11/509,783, dated Jan. 31, 2008, 9 pages.
In the U.S. Patent and Trademark Office, Final Office Action in re: U.S. Appl. No. 11/509,783, dated Oct. 21, 2008, 5 pages.
In the U.S. Patent and Trademark Office, Final Office Action in re: U.S. Appl. No. 10/130,783, dated Jan. 27, 2006, 13 pages.
In the U.S. Patent and Trademark Office, Non-Final Office Action in re: U.S. Appl. No. 10/130,783, dated Apr. 29, 2005, 9 pages.
In the U.S. Patent and Trademark Office, Non-Final Office Action in re: U.S. Appl. No. 10/398,134, dated Jan. 18, 2006, 8 pages.
In the U.S. Patent and Trademark Office, Non-Final Office Action in re: U.S. Appl. No. 10/398,134, dated May. 12, 2005, 11 pages.
In the U.S. Patent and Trademark Office, Non-Final Office Action in re: U.S. Appl. No. 10/398,134, dated Oct. 17, 2006, 14 pages.
In the U.S. Patent and Trademark Office, Non-Final Office Action in re: U.S. Appl. No. 10/473,821, dated Aug. 29, 2005, 12 pages.
In the U.S. Patent and Trademark Office, Non-Final Office Action in re: U.S. Appl. No. 10/473,821, dated Mar. 24, 2008, 9 pages.
In the U.S. Patent and Trademark Office, Non-Final Office Action in re: U.S. Appl. No. 10/473,821, dated May. 2, 2006, 8 pages.
In the U.S. Patent and Trademark Office, Final Office Action in re: U.S. Appl. No. 10/473,821, dated Dec. 31, 2008, 5 pages.
In the U.S. Patent and Trademark Office, Final Office Action in re: U.S. Appl. No. 10/473,821, dated Jan. 19, 2007, 10 pages.
In the U.S. Patent and Trademark Office, Final Office Action in re: U.S. Appl. No. 10/516,733, dated Jun. 17, 2008, 9 pages.
In the U.S. Patent and Trademark Office, Non-Final Office Action in re: U.S. Appl. No. 10/516,733, dated Feb. 26, 2009, 4 pages.
In the U.S. Patent and Trademark Office, Non-Final Office Action in re: U.S. Appl. No. 10/516,733, dated Feb. 5, 2007, 7 pages.
In the U.S. Patent and Trademark Office, Non-Final Office Action in re: U.S. Appl. No. 10/516,733, dated Sep. 12, 2007, 7 pages.
In the U.S. Patent and Trademark Office, Non-Final Office Action in re: U.S. Appl. No. 11/601,691, dated Apr. 3, 2009, 29 pages.
In the U.S. Patent and Trademark Office, Final Office Action in re: U.S. Appl. No. 10/558,617, dated Jan. 30, 2008, 8 pages.
In the U.S. Patent and Trademark Office, Final Office Action in re: U.S. Appl. No. 10/558,617, dated Jun. 26, 2009, 14 pages.
In the U.S. Patent and Trademark Office, Non-Final Office Action in re: U.S. Appl. No. 10/558,617, dated Dec. 22, 2008, 8 pages.
In the U.S. Patent and Trademark Office, Non-Final Office Action in re: U.S. Appl. No. 10/558,617, dated Jun. 29, 2007, 10 pages.
In the U.S. Patent and Trademark Office, Final Office Action in re: U.S. Appl. No. 09/856,378, dated Jan. 28, 2003, 11 pages.
In the U.S. Patent and Trademark Office, Final Office Action in re: U.S. Appl. No. 09/856,378, dated Sep. 27, 2002, 7 pages.
In the U.S. Patent and Trademark Office, Final Office Action in re: U.S. Appl. No. 10/398,133, dated Mar. 24, 2009, 8 pages.
In the U.S. Patent and Trademark Office, Non-Final Office Action in re: U.S. Appl. No. 10/398,133, dated Jun. 13, 2008, 13 pages.
In the U.S. Patent and Trademark Office, Non-Final Office Action in re: U.S. Appl. No. 10/398,133, dated Nov. 4, 2005, 10 pages.

In the U.S. Patent and Trademark Office, Non-Final Office Action in re: U.S. Appl. No. 10/398,133, dated Sep. 28, 2007, 15 pages.
In the U.S. Patent and Trademark Office, Non-Final Office Action in re: U.S. Appl. No. 10/398,133, dated Aug. 17, 2009, 8 pages.
In the U.S. Patent and Trademark Office, Non-Final Office Action in re: U.S. Appl. No. 10/574,475, dated Jan. 31, 2008, 9 pages.
In the U.S. Patent and Trademark Office, Non-Final Office Action in re: U.S. Appl. No. 10/574,475, dated Nov. 7, 2008.
In the U.S. Patent and Trademark Office, Final Office Action in re: U.S. Appl. No. 08/621,438, dated Apr. 22, 1998, 1 pages.
In the U.S. Patent and Trademark Office, Non-Final Office Action in re: U.S. Appl. No. 08/621,438, dated Feb. 13, 1997, 4 pages.
In the U.S. Patent and Trademark Office, Non-Final Office Action in re: U.S. Appl. No. 08/621,438, dated Jul. 24, 1997, 5 pages.
In the U.S. Patent and Trademark Office, Non-Final Office Action in re: U.S. Appl. No. 10/580,035, dated Dec. 3, 2008, 25 pages.
In the U.S. Patent and Trademark Office, Final Office Action in re: U.S. Appl. No. 10/580,035, dated Aug. 7, 2009, 16 pages.
Akiyoshi et al., "Self-Assembled Hydrogel Nanoparticle of Cholesterol-Bearing Pullulan as a Carrier of Protein Drugs: Complexation and Stabilization of Insulin," J. Control. Release, 1998; 54, pp. 313-320.
Akiyoshi et al., "Stabilization of Insulin upon Supramolecular Complexation with Hydrophobized Polysaccharide Nanoparticle," Chemistry Letters, 1995; 8:707-708.
Candau, S., Chapter 3: Light Scattering, *Surfactant Solutions*, vol. 22, Ed. R. Zana, M. Dekker, Inc., NY (1984) p. 147-207.
Database WPI Week 200274, AN 2002-685440, Derwent Publications Ltd., London, GB, 2002.
Database WPI Week 200355, AN 2002-694010, Derwent Publications Ltd., London, GB, 2002.
Database WPI Week 200644, AN 2002-260230, Derwent Publications Ltd., London, GB, 2002.
Davies, J.T., "A Quantitative Kinetic Theory of Emulsion Type, I. Physical Chemistry of the Emulsifying Agent," *Proceedings of the Second Interntional Congress of Surface Activity*, 1957; pp. 426-439.
Handbook of Chemistry and Physics, 88th Ed., 2008 (Viscosities of Liquids) Section 6, pp. 175-179.
Harada et al., "Formation of Polyion Complex Micelles in an Aqueous Milieu from a Pair of Oppositely-Charged Block Copolymers with Poly(ethylene glycol) Segments," *Macromolecules*, 1995, vol. 28, pp. 5294-5299.
Hudecz et al., "Branched Polypeptides with a POLY-(L-Lysine) Backbone: Synthesis, Conformation, and Immunomodulation," *Polymeric Materials in Medication*, Plenum Press, New York, 1985; pp. 265-289.
Illum et al., "Effect of the Nonionic Surfactant Poloxamer 338 on the Fate and Deposition of Polystyrene Microspheres Following Intravenous Administration," *J. Pharm. Sci.*, 1983; 72:9, pp. 1086-1089.
Jaworek et al., "Effects of Analogs of (pyro)Glu-His-Gly-OH on Food Consumption and Gastric Acid Secretion in Rats," *Life Science*, 1984; 34:26, pp. 2597-2603.
Kataoka, K. "Preparation of Novel Drug Carrier based on the Self-Association of Block Copolymer," Drug Delivery System, 1995, vol. 10, No. 5, pp. 363-370.
Kuroda et al., "Hierarchical Self-Assembly of Hydrophobically Modified Pullulan in Water: Gelation by Networks of Nanoparticles," *Langmuir*, 2002; 18, pp. 3780-3786.
Maa et al., "Spray-Drying of Air-Liquid Interface Sensitive Recombinant Human Growth Hormone, "*J. Pharm. Sci.*, 1988; 87:2, pp. 152-159.
Mezo et al., "Synthesis and Conformational Studies of Poly(L-Lysine) Based Branched Polypeptides with Ser and Glu/Leu in the Side Chains," *J. Controlled Release*, 2000; 63, pp. 81-95.
Oppenheim et al., "The Primary Structure and Functional Characterization of the Neutral Histidine-Rich Polypeptide from Human Parotid Secretion," *Journal of Biological Chemistry*, 1986; 261:3, pp. 1177-1182.
Shen, W.C., "Acid Sensitive Dissociation Between Poly (Lysine) and Histamine-Modified Poly (Glutamate) as a Model for Drug-Releasing From Carriers in Endosomes," *Biochim. Biophys. Acts.*, 1990, 1034(1): 122-124.

Tsutsumiuchi et al., "Synthesis of Polyoxazoline-(Glyco)peptide Block Copolymer by Ring-Opening Polymerization of (Sugar-Substituted) α-Amino Acid N-Carboxyanhydrides with Polyoxazoline Macroinitiators," Macromolecules, 1997; 30:4013-4017.

Van Heeswijk et al., "The Synthesis and Characterization of Polypeptide-Adriamycin Conjugates and its Complexes with Adriamycin," *J. Controlled Release*, 1985; 1:4, pp. 301-315.

Volgler et al., *Helv. Chim. Acta*, 47: 525-544 (1964).

Woodle et al., "Sterically Stabilized Liposomes," *Biochim. Biophys. Acta*, 1992; 1113:2, pp. 171-199.

Woodle, M.C., "Controlling Liposome Blood Clearance by Surface-Grafted Polymers," *Adv. Drug Deliv. Rev.*, 1998; 32:1-2, pp. 139-152.

Yokoyama et al., "Incorporation of Water-Insoluble Anticancer Drug into Polymeric Micelles and Control of Their Particle Size," *J. Controlled Release*, 1998; 55:219-229.

In the U.S. Patent and Trademark Office Final Office Action in re: U.S. Appl. No. 10/580,037, dated Apr. 27, 2011, 23 pages.

In the U.S. Patent and Trademark Office Restriction/Election Requirement in re: U.S. Appl. No. 10/580,037, dated Oct. 1, 2009, 7 pages.

In the U.S. Patent and Trademark Office Restriction/Election Requirement in re: U.S. Appl. No. 10/580,035, dated Mar. 5, 2008, 6 pages.

In the U.S. Patent and Trademark Office Final Office Action in re: U.S. Appl. No. 10/580,035, dated Dec. 16, 2010, 9 pages.

Ferry et al, "Viscoelastic Properties of Polymers," *J. Wiley, NY*, 1980: 332 pages.

International Search Report for related International Application No. PCT/FR2004/050605, dated Mar. 16, 2005.

International Search Report for related International Application No. PCT/FR2004/050603, dated Mar. 16, 2005.

International Search Report for related International Application No. PCT/FR2004/050607, dated Apr. 13, 2006.

"Viscosities of Liquids," *Handbook of Chemistry and Physics*, 2008; 88:Section 6: pp. 175-179.

INPADOC Patent Family for WO 00/30618, [online], accessed Nov. 28, 2008, 2 pages. Retrieved from the Internet: < URL:http://v3.espacenet.com/inpadoc?submitted=true&CC=WO&NR=0030618&KC=&FT=E>.

* cited by examiner

PHARMACEUTICAL FORMULATIONS FOR THE PROLONGED RELEASE OF ACTIVE PRINCIPLE(S) AND THEIR APPLICATIONS

The present invention relates to novel pharmaceutical formulations based on stable, fluid aqueous colloidal suspensions for the prolonged release of active principle(s), particularly protein and peptide active principle(s), and to the applications, especially therapeutic applications, of these formulations.

These active pharmaceutical formulations are of interest in both human and veterinary therapeutics.

In the field of the prolonged release of pharmaceutical active principles, especially therapeutic proteins, there is a need in many cases to ensure as far as possible that the patient's plasma protein or peptide concentration is close to the value observed in the healthy subject.

This objective is compromised by the short life of proteins in the plasma, which makes it necessary to inject the therapeutic protein repeatedly. The plasma concentration of therapeutic protein then has a "sawtooth" profile characterized by high concentration peaks and very low concentration minima. The concentration peaks, which are very much greater than the basal concentration in the healthy subject, have very pronounced harmful effects due to the high toxicity of therapeutic proteins such as the interleukin IL2. Furthermore, the concentration minima are below the concentration that is necessary to have a therapeutic effect, so the patient receives poor therapeutic cover and suffers serious long-term side effects.

Also, to ensure that the patient's plasma concentration of therapeutic protein is close to the ideal value for the patient's treatment, the pharmaceutical formulation in question has to allow the prolonged release of the therapeutic protein so as to limit the variations in plasma concentration over time.

Furthermore, this active formulation should preferably meet the following specifications already familiar to those skilled in the art:

1—prolonged release of an active and non-denatured therapeutic protein, for example a human or synthetic protein, so that the plasma concentration is maintained at the therapeutic level;
2—liquid form sufficiently fluid to be easily injectable and sterilizable by filtration on filters with a pore size less than or equal to 0.2 micron;
3—stable liquid form;
4—biocompatibility and biodegradability;
5—non-toxicity;
6—non-immunogenicity;
7—excellent local tolerance.

Several approaches have already been proposed in the prior art in an attempt to achieve these objectives.

In the first approach, the native therapeutic protein is modified by the covalent grafting of one or more polymer chains or by the covalent grafting of a protein such as human serum albumin (HSA). The protein modified in this way has a lower affinity for its receptors and its half-life in the general circulation increases considerably. The amplitude of the variation in concentration between the plasma protein concentration peaks and troughs is thereby considerably reduced. Thus an interferon alpha 2b chemically modified by the grafting of a polyethylene glycol chain of molecular weight 12 kD is marketed by Shering Plough under the name VIRAFÉRON® PEG. The effect of this chemical modification is to increase the half-life in the patient from 6.8 to 33 hours. In general terms this step of chemical modification of the therapeutic protein has two major disadvantages. Firstly, the irreversible modification of the protein, which, now no longer being a human protein, can lead to toxicity and immunogenicity problems in the long term. The second disadvantage stems from the partial loss of bioactivity of the modified therapeutic protein.

In a second approach, it has been proposed to increase the duration of action by using formulations containing at least one polymer and one active principle which are liquid at ambient temperature and in the ambient atmosphere, are injectable and become more viscous after injection, for example under the effect of a change in pH and/or temperature.

Thus, in this vein, patent U.S. Pat. No. 6,143,314 discloses an organic polymer solution for the controlled release of AP that forms a solid implant after injection. This solution comprises:

(A) 10 to 80% by weight of a base thermoplastic polymer which is biocompatible, biodegradable and insoluble in water or the physiological fluids (for example a polylactic and/or polyglycolic polymer);
(B) an organic solvent, such as N-methylpyrrolidone, which disperses in the physiological fluids;
(C) an active principle (AP);
(D) and finally 1 to 50% by weight of a controlled release agent consisting of a block copolymer of the polylactic-glycolic/polyethylene glycol type.

After injection, (B) disperses or dissipates in the physiological fluids. (A) forms an implant that encapsulates (C), which is not covalently bonded to either (A) or (D) and is thus released slowly in vivo.

The main disadvantage of this technique is the use of an organic solvent (B), which is potentially denaturing for the AP (C) (e.g. therapeutic proteins) and toxic to the patient. In addition, in vivo hydrolysis of the polymer (A) generates an acid capable of causing problems of local tolerance.

PCT applications WO-A-99/18142 and WO-A-00/18821 relate to aqueous polymer solutions which contain an AP in dissolved or colloidal form, can be administered to warm-blooded animals, especially by injection, and form a gelled deposit of AP (e.g. insulin) in vivo because the physiological temperature is above their gelling point. The gel formed in this way releases the AP in a prolonged manner. These particular biodegradable polymers are ABA or BAB tri-blocks, where A=polylactic-glycolic copolymer (PLAGA) or poly-lactic polymer (PLA) and B=polyethylene glycol. The liquid ⇒gel transformation temperatures of these tri-block polymers are e.g. 36, 34, 30 and 26° C. Like the polymers (A) according to U.S. Pat. No. 6,143,314, in vivo hydrolysis of these ABA or BAB tri-block polymers produces acids which may not have the correct local tolerance.

PCT application WO-A-98/11874 describes pharmaceutical formulations comprising a lipophilic active principle, a gelling polymer (Gelrite®=deacetylated gellan gum or ethylhydroxy cellulose) and a surfactant. The polymer/surfactant interaction, and perhaps only the presence of electrolytes, such as $Ca^{++}$ ions, in a physiological concentration, in the case of the polymer Gelrite®, leads to the formation of a gel consisting of a polymer/surfactant aggregate, to which the lipophilic active principle bonds non-covalently. This formulation is intended for local administration to a target organ (e.g. the eye). The aggregate/active principle association which forms in situ allows the slow release of the active principle into the target organ.

A third approach adopted in an attempt to prolong the duration of action of a protein while preserving its bioactivity was to use a non-denatured therapeutic protein and incorporate it in microspheres or implants based on biocompatible polymers. This approach is illustrated especially by patent U.S. Pat. No. 6,500,448 and patent application US-A-2003/0133980, which describe a composition for the prolonged release of human growth hormone (hGH) in which the hormonal protein is first stabilized by complexation with a metal and then dispersed in a biocompatible polymer matrix. The biocompatible polymer is e.g. a polylactide, a polyglycolide or a poly(lactide-co-glycolide) copolymer. The composition is presented e.g. in the form of a suspension of microspheres in a solution of sodium carboxymethyl cellulose. This approach has several disadvantages: first of all, during the microsphere manufacturing process the protein is brought into contact with potentially denaturing organic solvents. Also, the microspheres are large (1 to 1000 microns), which is restricting in terms of injection and ease of sterilization on filters. Finally, problems of local tolerance can arise when the polymer is hydrolysed in situ.

According to a fourth approach, forms for the prolonged release of a therapeutic protein have been developed which consist of low-viscosity liquid suspensions of nanoparticles loaded with therapeutic proteins. These suspensions have made it possible to administer native therapeutic proteins easily.

A first form of prolonged-release nanoparticle suspensions consists of suspensions of liposomes in which the unmodified native therapeutic protein is encapsulated. After injection, the protein is released from the liposomes gradually, prolonging the time for which the protein is present in the general circulation. Thus, for example, in the article *Cancer Res.*, 43, p. 546, 1983, Frossen et al. describe the encapsulation of antineoplastic agents in liposomes in order to enhance their therapeutic efficacy. However, the release of the drug is too rapid to give a true prolonged release. In its patent U.S. Pat. No. 5,399,331, Liposome Company, Inc. proposes to improve the in vitro release time of interleukin 2 by grafting it covalently to the liposome. So, said method suffers from the same shortcomings as the "modified protein" approach referred to above.

To overcome the lack of stability of liposomes while at the same time retaining the advantages of a liquid nanoparticle formulation of low viscosity, Flamel Technologies has proposed another method, in which the therapeutic protein is associated with nanoparticles of a water-soluble polyamino acid that is "hydrophobically modified", i.e. modified by the grafting of hydrophobic groups. This polymer is selected in particular from polyamino acids (polyglutamates or polyaspartates) carrying hydrophobic grafts.

One of the notable advantages of these hydrophobically modified polymers is that they spontaneously self-assemble in water to form nanoparticles.

Another advantage of these systems is that the proteins or peptides, particularly therapeutic proteins, associate spontaneously with the nanoparticles of hydrophobically modified polymers. This association is non-covalent and takes place without recourse either to a surfactant or to a potentially denaturing transformation process. It does not entail encapsulation of the protein in a microsphere, as disclosed in patent U.S. Pat. No. 6,500,448 and patent application US-A-2003/0133980. In total contrast, these nanoparticles of hydrophobically modified copolyamino acids spontaneously adsorb the proteins in solution without chemically modifying them or denaturing them and without subjecting them to aggressive treatment steps such as "emulsification" and "solvent evaporation". The formulations can be stored in liquid or lyophilized form.

After injection, for example subcutaneously, these suspensions of nanoparticles loaded with proteins gradually release the bioactive non-denatured protein in vivo. Such non-covalent associations of protein active principle (AP)/poly[Glu] or poly[Asp] are disclosed in patent application WO-A-00/30618.

Said patent application particularly describes colloidal suspensions of pH 7.4 comprising associations of human insulin with nanoparticles of "hydrophobically modified" polyglutamate. The Table below shows the "hydrophobically modified" polyamino acids used and the degrees of association obtained in the Examples of WO-A-00/30618.

| EXAMPLE | POLYMER | Degree of association (%) |
|---|---|---|
| 1 | poly[(Glu-O-Na)$_{0.63}$-block-(Glu-O-methyl)$_{0.37}$] | 55 |
| 2 | poly[(Glu-O-Na)$_{0.66}$-block-(Glu-O-ethyl)$_{0.34}$] | 26 |
| 3 | poly[(Glu-O-Na)$_{0.65}$-block-(Glu-O-hexadecyl)$_{0.35}$] | 36 |
| 4 | poly[(Glu-O-Na)$_{0.88}$-block-(Glu-O-dodecyl)$_{0.12}$] | >90 |

These colloidal suspensions contain 1.4 mg/ml of insulin and 10 mg/ml of "hydrophobically modified" polyamino acid.

FIG. 1 of WO-A-00/30618 shows that the in vivo release time of the insulin vectorized by the above-mentioned suspensions is 12 h. This release time could profitably be increased.

Thus, even though said PCT application already represents a considerable advance, its technical content can be further optimized in respect of the specifications listed above, and especially as regards lengthening of the in vivo release time.

Unpublished French patent applications no. 02 07008 of Jun. 7, 2002, 02 09670 of Jul. 30, 2002, 03 50190 of May 28, 2003 and 03[1] 50641 of Oct. 3, 2003 relate to novel water-soluble amphiphilic polyatmino acids comprising aspartic units and/or glutamic units, in which at least some of these units carry hydrophobic grafts. Like the hydrophobically modified polyamino acids disclosed in patent application WO-A-00/30618, these novel polymer starting materials spontaneously form, in an aqueous liquid medium, colloidal suspensions of nanoparticles which can be used for the prolonged release of AP (insulin). They are biocompatible and biodegradable and proteins, particularly therapeutic proteins, absorb spontaneously onto these nanoparricles without undergoing chemical modification or denaturation.

Said patent applications further relate to novel pharmaceutical, cosmetic, dietetic or phytosanitary compositions based on these polyamino acids.

The amphiphilic "hydrophobically modified" polyamino acids according to French patent application no. 02 07008 comprise aspartic units and/or glutamic units carrying hydrophobic grafts containing at least one alpha-tocopherol unit, e.g. polyglutamate or polyaspartate grafted with alpha-tocopherol of synthetic or natural origin.

Said unpublished patent application specifically discloses a colloidal suspension which contains nanoparticles formed of polymer/active protein associations and which is obtained by mixing 1 mg of a polyglutamate grafted with alpha-tocopherol and 7 mg of insulin in 1 ml of water at pH 7.0.

The amphiphilic "hydrophobically modified" polyamino acids according to French patent application no. 02 09670 comprise aspartic units and/or glutamic units carrying hydrophobic grafts that contain at least one hydrophobic unit and are joined to the aspartic and/or glutamic units via a rotating linkage containing two amide groups, and more precisely via a "spacer" of the lysine or ornithine type.

Said unpublished patent application specifically discloses a colloidal suspension which contains nanoparticles formed of polymer/active protein associations and which is obtained by mixing 10 mg of a polyglutamate grafted with palmitic acid via a lysine "spacer" and 200 IU of insulin (7.4 mg) in 1 ml of water at pH 7.4.

The amphiphilic "hydrophobically modified" polyamino acids according to French patent application no. 03 50190 comprise aspartic units and/or glutamic units, some of which carry at least one graft joined to an aspartic or glutamic unit via an "amino acid" "spacer" based on Leu and/or ILeu and/or Val and/or Phe, a C6-C30 hydrophobic group being joined to the "spacer" via an ester linkage.

Said unpublished patent application specifically discloses a colloidal suspension which contains nanoparticles formed of polymer/active protein associations and which is obtained by mixing an aqueous solution containing 10 mg of a polyglutamate grafted with a -Leu-OC8, -Val-OC12 or -Val-cholesteryl graft and 200 IU of insulin (7.4 mg) per millilitre of water at pH 7.4.

French patent application no. 03 50641 discloses anionic, amphiphilic linear homopolyamino acids comprising aspartic units or glutamic units, the ends of which carry hydrophobic groups containing from 8 to 30 carbon atoms.

In particular, the "hydrophobically modified" telechelic homopolyamino acids are e.g. a poly[GluONa] with PheOC18/C18 ends or a poly[GluONa] with PheOC 18/alpha-tocopherol ends. Said unpublished patent application also describes a colloidal suspension which contains nanoparticles formed of polymer/active protein associations and which is obtained by mixing 10 mg of one of the above-mentioned polymers and 200 IU of insulin (7.4 mg) per millilitre of water at pH 7.4.

The in vivo release time of the insulin "vectorized" by the suspensions according to said unpublished patent applications could profitably be increased.

Whatever the case may be, none of this prior art relating to colloidal suspensions of nanoparticles of hydrophobically modified polyamino acids discloses a formulation that makes it possible to:
(I) sufficiently increase the release time of the active protein after parenteral injection, particularly subcutaneous injection;
(II) and/or reduce the plasma concentration peak of the active protein after injection of the formulation containing it.

Under these conditions, one of the essential objects of the present invention is therefore to propose a liquid pharmaceutical formulation for the prolonged release of active principle (s) which overcomes the deficiencies of the prior art and, in particular, makes it possible after parenteral (e.g. subcutaneous) injection to obtain a prolonged in vivo release time for non-denatured active principles (AP) (e.g. therapeutic proteins and peptides and small molecules), for example human or synthetic proteins.

Another essential object of the invention is to propose a liquid pharmaceutical formulation for the prolonged release of AP in vivo which is sufficiently fluid to be easily injectable and sterilizable by filtration on filters with a pore size less than or equal to 0.2 micron.

Another essential object of the invention is to propose a liquid pharmaceutical formulation for the prolonged release of AP in vivo which is stable on storage in both physicochemical and biological terms.

Another essential object of the invention is to propose a liquid pharmaceutical formulation for the prolonged release of AP in vivo which has at least one of the following properties: biocompatibility, biodegradability, atoxicity, good local tolerance.

Another essential object of the invention is to propose a pharmaceutical formulation for the slow prolonged release of AP in vivo, this formulation being an aqueous colloidal suspension of low viscosity comprising submicronic particles of polymer PO that are auto-associated with at least one AP, the polymer PO being a water-soluble biodegradable polymer carrying hydrophobic groups.

Another essential object of the invention is to propose a pharmaceutical formulation for the slow prolonged release of AP in vivo, this formulation being an aqueous colloidal suspension of low viscosity comprising submicronic particles of polymer PO that are auto-associated with at least one AP, the polymer PO being e.g. a polyamino acid formed of aspartic units and/or glutamic units, at least some of these units carrying grafts containing at least one hydrophobic group (HG), PO also being biodegradable, water-soluble and amphiphilic.

Another essential object of the invention is to propose derived products and/or precursors of the formulation referred to in the objects listed above.

It is particularly to the Applicant's credit to have developed aqueous liquid pharmaceutical formulations of low viscosity at the physiological temperature which, surprisingly, form a gelled deposit in vivo after easy parenteral administration to humans or warm-blooded mammals, the formation of this deposit not being triggered by a change in pH or temperature on parenteral injection, or by the presence of electrolyte(s) (such as $Ca^{++}$ ions) in a physiological concentration, and/or of at least one surfactant, or by the dispersion of an organic solvent in the physiological medium. The gelled deposit formed in this way significantly increases the in vivo release time of the AP.

The invention thus relates to a liquid pharmaceutical formulation for the prolonged release of active principle(s) (AP), this formulation comprising an aqueous colloidal suspension of low viscosity based on submicronic particles of water-soluble biodegradable polymer (PO) carrying hydrophobic groups (HG), said particles being non-covalently associated with at least one active principle (AP), characterized in that:
the dispersion medium of the suspension consists essentially of water,
said formulation is capable of being injected parenterally and then forming a gelled deposit in vivo, this formation of a gelled deposit:
on the one hand being at least partly caused by at least one physiological protein present in vivo,
and on the other hand making it possible to prolong and control the in vivo release time of the AP beyond 24 h after administration,
it is liquid under the injection conditions,
and it is also liquid at the physiological temperature and/or physiological pH and/or in the presence of:
a physiological electrolyte in a physiological concentration,
and/or at least one surfactant.

Advantageously, this gelling in vivo does not result from a change in pH and/or temperature, or from the presence of electrolytes (e.g. Ca++) in a physiological concentration, and/or of at least one surfactant, or from the dispersion in vivo of one or more organic solvents that may be present in the injected formulation.

Without wishing to be bound by theory, one may consider that the physiological proteins present in vivo in physiological concentrations allow aggregation of the nanoparticles of PO associated with at least one AP. Such gelling takes place e.g. in one hour or more, 24 h, 48 h or 72 h, inter alia.

In an optimized embodiment of the invention, the concentration of [PO] in the formulation is set at a sufficiently high value to allow the formation of a gelled deposit in vivo after parenteral injection, in the presence of at least one physiological protein.

According to one mode of definition, which is based not on an in vivo behaviour, as indicated above, but on an in vitro behaviour, the invention relates to a liquid pharmaceutical formulation for the prolonged release of active principle(s)
 being liquid in the ambient atmosphere,
 also being liquid at the physiological temperature and/or physiological pH and/or in the presence of:
  a physiological electrolyte in a physiological concentration,
  and/or at least one surfactant,
 and comprising an aqueous colloidal suspension of low viscosity based on submicronic particles of water-soluble biodegradable polymer PO carrying hydrophobic groups HG, said particles being non-covalently associated with at least one active principle AP, and the dispersion medium of the suspension consisting essentially of water,
characterized in that its concentration of [PO] is set at a sufficiently high value to allow the formation of a gelled deposit in vitro, in the presence of at least one protein.

Preferably, the liquid pharmaceutical formulation according to the invention is characterized in that its concentration of [PO] is such that:
 $[PO] \geq 0.9 \cdot C1$,
 preferably $20 \cdot C1 \geq [PO] \geq C1$,
 and particularly preferably $10 \cdot C1 \geq [PO] \geq C1$,
where C1 is the "induced gelling" concentration of the particles of PO, as measured in an IG test.

The gelled deposit obtained after parenteral injection of the formulation allows a valuable prolongation of the release time of the AP (e.g. therapeutic protein), as well as a reduction in the plasma concentration peak.

The release time of the AP is significantly increased compared with that of the formulations of the prior art, particularly those described in published PGT application WO-A-00/30618 and unpublished French patent applications no. 02 07008, 02 09670, 03 50190 and 03 50641.

The prolongation of the in vivo release time of AP induced by the formulations according to the invention is all the more valuable because the AP (e.g. therapeutic proteins) are still fully bioactive and non-denatured.

Throughout the present disclosure, the supramolecular arrangements of polymer PO associated or not associated with the AP will be arbitrarily referred to as "submicronic particles" or "nanoparticles". These correspond to (liquid or solid) particles with a mean hydrodynamic diameter (measured by the Md procedure defined below in the Examples) of e.g. between 1 and 500 nm and procedure defined below in the Examples) of e.g. between 1 and 500 nm and preferably of between 5 and 250 nm.

Moreover, it is very important to note that these formulations are liquid, i.e. they advantageously have a very low viscosity, making them easy to inject. They only gel in vivo.

According to the invention, the qualifications "liquid", "low viscosity" or "very low viscosity" advantageously correspond to a dynamic viscosity less than or equal to 5 Pa·s at 20° C. The reference measurement for the viscosity can be made e.g. at 20° C. using an AR1000 rheometer (TA Instruments) equipped with a cone-and-plate geometry (4 cm, 2°). The viscosity v is measured for a shear gradient of $10\ s^{-1}$.

Thus the viscosity of the formulations according to the invention can be e.g. between $1 \cdot 10^{-3}$ and 5 Pa·s, preferably between $1 \cdot 10^{-3}$ and 0.8 Pa·s and particularly preferably between $1 \cdot 10^{-3}$ and 0.5 Pa·s.

This low viscosity makes the formulations of the invention not only easy to inject parenterally, particularly intramuscularly or subcutaneously, inter alia, but also easy to sterilize at reduced cost by filtration on sterilization filters with a pore size of 0.2 μm.

This liquid state or low viscosity of the formulations of the invention exists both at injection temperatures corresponding to ambient temperatures, for example of between 4 and 30° C., and at the physiological temperature.

The formulation according to the invention is preferably an aqueous colloidal suspension of nanoparticles associated with one or more AP. This means that, according to the invention, the dispersion medium of this suspension is formed essentially of water. In practice, this water represents e.g. at least 50% by weight, based on the total weight of the formulation.

In terms of the invention, the word "protein" denotes either a protein or a peptide, it being possible for this protein or peptide to be unmodified or modified e.g. by the grafting of one or more polyoxyethylene groups.

"Physiological proteins" are understood in terms of the invention as meaning the endogenous proteins and/or peptides of warm-blooded mammals that are present at the injection site.

"Physiological temperature" is understood in terms of the invention as meaning the physiological temperature of warm-blooded mammals, namely e.g. about 37-42° C.

"Physiological pH" is understood in terms of the invention as meaning a pH e.g. of between 6 and 7.6.

"Gel" is understood in terms of the invention as meaning a semisolid state into which the liquid formulation according to the invention is transformed spontaneously only by the presence of physiological protein(s), without the essential intervention of the physiological pH and/or the physiological temperature and/or the presence of a physiological electrolyte (e.g. $Ca^{++}$) and/or the dispersion (or dissipation) in vivo of an organic solvent that may be present in the injected formulation.

"Physiological electrolyte" is understood in terms of the invention as meaning any electrolyte species (for example $Ca^{++}$ ions) present in warm-blooded mammals.

"Physiological concentration" is understood in terms of the invention as meaning any physiological concentration encountered in warm-blooded mammals for the physiological medium in question.

In addition, the formulations according to the invention are non-toxic, have a good local tolerance and are stable.

It is also to the inventors' credit to have developed an in vitro IG test for selecting a population of preferred formulations according to the invention and determining the appropriate concentrations of PO in the formulations.

According to the invention, the IG test for measuring the gelling concentration C1 is a reference test for defining the critical concentration C1, hereafter called the induced gelling concentration C1, which characterizes each colloidal formulation according to the invention.

The IG test for determining the induced gelling concentration C1 is as follows:

The concentration C1 is determined by preparing colloidal formulations having variable concentrations of amphiphilic polymer according to the invention and a constant concentration of therapeutic protein. To this end, increasing amounts of dry powdered polymer are dissolved in deionized water. The solutions are kept at 25° C. for 16 hours, with magnetic stirring, before being mixed with a concentrated solution of therapeutic protein. The volume and concentration of this solution of therapeutic protein are adjusted to give the desired protein concentration for the formulation [for example 0.3 mg/ml of interferon alpha 2b or 2.5 mg/ml of interleukin 2 (IL2)].

The colloidal formulations prepared in this way are mixed with a concentrated aqueous solution of bovine serum albumin (BSA) containing 30 mg/ml, and then centrifuged for 15 minutes at 3000 rpm. The mixtures are stirred gently for 24 h and then recovered for characterization.

The viscoelasticity measurements are made on a TA Instruments AR1000 rheometer equipped with a cone-and-plate geometry (diameter 4 cm and angle 1.59°). A deformation of 0.01 rad, situated in the linear viscoelasticity domain, is imposed sinusoidally over a frequency range of between 0.1 and 300 rad/s. The temperature of the sample is kept constant at 20° C. by means of a Peltier cell.

The frequency spectra of the modulus of elasticity G' and the modulus of viscosity or loss modulus G" make it possible to define the characteristic relaxation time Tr, which is defined here as the reciprocal of the frequency at which the modulus of elasticity G' intersects the modulus of viscosity G". A detailed account of these questions will be found in the work by Ferry entitled *Viscoelastic Properties of Polymers*, J. D. Ferry, J. Wiley, N.Y., 1980, and in the article by J. REGALADO et al., *Macromolecules*, 1999, 32, 8580.

Measurement of the relaxation time Tr as a function of the polymer concentration of the formulation makes it possible to define the concentration C1 at which this time Tr exceeds 1 second. Examples of values of the gelling concentration C1 will be given in Example 8 below.

Likewise, it is possible to define the concentrations C0.1 and C10 at which the relaxation time exceeds 0.1 s and 10 s, respectively. These concentrations are classed in the following increasing order: C0.1<C1<C10.

In one variant of the formulation according to the invention:

[PO]≧C0.1,
preferably [PO]≧C1,
and particularly preferably [PO]≧C10.

According to an advantageous additional characteristic: [PO]≦20.C1.

In terms of the invention and throughout the present disclosure, the words "association" and "associate" employed to qualify the relationships between one or more active principles and the polymers PO (for example the polyamino acids) denote in particular that the active principle(s) is (are) bonded to the polymer(s) PO [for example the polyamino acid(s)] non-covalently, for example by electrostatic and/or hydrophobic interaction and/or hydrogen bonding and/or steric hindrance.

The polymers PO according to the invention are water-soluble bio-degradable polymers carrying hydrophobic groups HG. The hydrophobic groups can be in reduced number relative to the rest of the chain and can be attached laterally to the chain or intercalated in the chain and be distributed randomly (random copolymer) or distributed in the form of sequences or grafts (block copolymers or sequenced copolymers).

Without implying a limitation, the hydrophobically modified polymers PO can be selected from the group comprising amphiphilic copolyamino acids, polysaccharides (preferably those in the subgroup comprising pullulans and/or chitosans and/or mucopolysaccharides), gelatins and mixtures thereof.

In one preferred embodiment of the invention, PO is selected from amphiphilic copolyamino acids.

In terms of the invention and throughout the present disclosure, the words "polyamino acid" cover both oligoamino acids comprising from 2 to 20 "amino acid" units and polyamino acids comprising more than 20 "amino acid" units.

Preferably, the polyamino acids according to the present invention are oligomers or homopolymers comprising glutamic or aspartic acid repeat units or copolymers comprising a mixture of these two types of "amino acid" units. The units in question in these polymers are amino acids having the D, L or D/L configuration and are bonded via their alpha or gamma positions in the case of the glutamate or glutamic unit and via their alpha or beta positions in the case of the aspartic or aspartate unit.

The preferred "amino acid" units of the main polyamino acid chain are those having the L configuration and a linkage of the alpha type.

In one particularly preferred embodiment of the invention, the polymer PO is a polyamino acid formed of aspartic units and/or glutamic units, at least some of these units carrying grafts containing at least one hydrophobic group HG. These polyamino acids are especially of the type described in PCT application WO-A-00/30618.

According to a first possibility, the PO of the formulation is (are) defined by general formula (1) below:

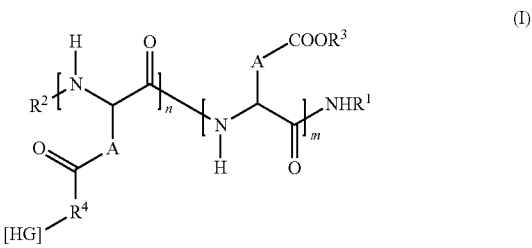

in which:
R$^1$ is H, a linear C2 to C10 alkyl or branched C3 to C10 alkyl, benzyl, a terminal amino acid unit or —R$^4$-[HG];
R$^2$ is H, a linear C2 to C10 acyl or branched C3 to C10 acyl group, a pyroglutamate or —R$^4$-[HG];
R$^3$ is H or a cationic entity preferably selected from the group comprising:
  metal cations advantageously selected from the subgroup comprising sodium, potassium, calcium and magnesium,
  organic cations advantageously selected from the subgroup comprising:
    cations based on amine,
    cations based on oligoamine,
    cations based on polyamine (polyethylenimine being particularly preferred),
    and cations based on amino acid(s) advantageously selected from the class comprising cations based on lysine or arginine,
  and cationic polyamino acids advantageously selected from the subgroup comprising polylysine and oligolysine;
R$^4$ is a direct bond or a "spacer" based on 1 to 4 amino acid units;
A independently is a radical —CH$_2$— (aspartic unit) or —CH$_2$—CH$_2$— (glutamic unit);

n/(n+m) is defined as the molar grafting rate and its value is sufficiently low for PO, dissolved in water at pH 7 and at 25° C., to form a colloidal suspension of submicronic particles of PO, n/(n+m) preferably being between 1 and 25 mol % and particularly preferably between 1 and 15 mol %;

n+m is defined as the degree of polymerization and varies from 10 to 1000 and preferably between 50 and 300;

HG is a hydrophobic group.

According to a second possibility, the PO of the formulation has (have) one of general formulae (II), (III) and (IV) below:

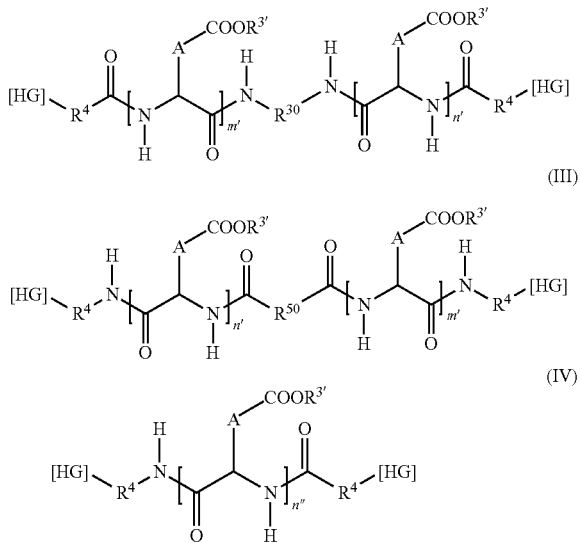

in which:
HG is a hydrophobic group;
R$^{30}$ is a linear C2 to C6 aLkyl group;
R$^{3'}$ is H or a cationic entity preferably selected from the group comprising:
  metal cations advantageously selected from the subgroup comprising sodium, potassium, calcium and magnesium,
  organic cations advantageously selected from the subgroup comprising:
    cations based on amine,
    cations based on oligoamine,
    cations based on polyamine (polyethylenimine being particularly preferred),
    and cations based on amino acid(s) advantageously selected from the class comprising cations based on lysine or arginine,
    and cationic polyamino acids advantageously selected from the subgroup comprising polylysine and oligolysine;
R$^{50}$ is a C2 to C6 alkyl, dialkoxy or diamine group;
R$^4$ is a direct bond or a "spacer" based on 1 to 4 amino acid units;
A independently is a radical —CH$_2$— (aspartic unit) or —CH$_2$—CH$_2$— (glutamic unit);
n'+m' or n" is defined as the degree of polymerization and varies from 10 to 1000 and preferably between 50 and 300.

Advantageously, the HG of the PO each independently of one another are a monovalent radical of the groups below:

in which:
R$^5$ is a methyl (alanine), isopropyl (valine), isobutyl (leucine), sec-butyl (isoleucine) or benzyl (phenylalanine);
R$^6$ is a hydrophobic radical containing from 6 to 30 carbon atoms;
l varies from 0 to 6.

According to one noteworthy characteristic of the invention, all or some of the hydrophobic groups R$^6$ of the PO are independently selected from the group of radicals comprising:
  a linear or branched alkoxy containing from 6 to 30 carbon atoms and optionnally containing at least one heteroatom (preferably O and/or N and/or S) and/or at least one unit of unsaturation,
  an alkoxy containing 6 to 30 carbon atoms, having one or more fused carbocyclic rings and optionally containing at least one unit of unsaturation and/or at least one heteroatom (preferably O and/or N and/or S),
  an alkoxyaryl or an aryloxyalkyl having 7 to 30 carbon atoms and optionally containing at least one unit of unsaturation and/or at least one heteroatom (preferably O and/or N and/or S).

In practice and without implying a limitation, the hydrophobic radical R$^6$ of the graft of the PO is derived from an alcohol precursor selected from the group comprising octanol, dodecanol, tetradecanol, hexadecanol, octadecanol, oleyl alcohol, tocopherol and cholesterol.

In a first embodiment of the invention, the main chains of the polyamino acids are alpha-L-glutamate or alpha-L-glutamic homopolymers.

In a second embodiment of the invention, the main chains of the polyamino acids are alpha-L-aspartate or alpha-L-aspartic homopolymers.

In a third embodiment of the invention, the main chains of the polyamino acids are alpha-L-aspartate/alpha-L-glutamate or alpha-L-aspartic/alpha-L-glutamic copolymers.

Advantageously, the distribution of the aspartic and/or glutamic units of the main polyamino acid chain of the PO is such that the resulting polymer is either random or of the block type or of the multiblock type.

According to another mode of definition, the PO used in the formulation according to the invention has a molecular weight of between 2000 and 100,000 g/mol and preferably of between 5000 and 40,000 g/mol.

In one variant, the PO of the formulation according to the invention carries at least one graft of the polyalkylene glycol type bonded to a glutamate and/or aspartate unit.

Advantageously, this graft is of the polyalkylene glycol type has formula (V) below:

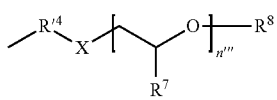

(V)

in which:
  $R'^4$ is a direct bond or a "spacer" based on 1 to 4 amino acid units;
  X is a heteroatom selected from the group comprising oxygen, nitrogen and sulfur;
  $R^7$ and $R^8$ independently are H or a linear C1 to C4 alkyl;
  $n'''$ varies from 10 to 1000 and preferably from 50 to 300.

In practice, the polyalkylene glycol is e.g. a polyethylene glycol.

It is desirable according to the invention for the molar percentage of polyalkylene glycol grafting to vary from 1 to 30%.

The polyamino acids PO are also extremely valuable in that, with an adjustable grafting rate, they disperse in water at pH 7.4 (e.g. with a phosphate buffer) to give colloidal suspensions.

Furthermore, active principles AP, such as proteins, peptides or small molecules, can associate spontaneously with nanoparticles comprising these polyamino acids PO.

It should be understood that the PO based on polyamino acids contain carboxyl groups which are either neutral (COOH form) or ionized (COO$^-$ anion), depending on the pH and the composition. For this reason, the solubility in an aqueous phase is a direct function of the proportion of free COOH groups in the PO (not grafted with the hydrophobic unit) and of the pH. In aqueous solution the countercation can be a metal cation such as sodium, calcium or magnesium, or an organic cation such as triethanolamine, tris(hydroxymethyl)aminomethane or a polyamine like polyethylenimine.

The PO of the polyamino acid type that are capable of being used in the formulation of the invention are obtained e.g. by methods known to those skilled in the art. Random polyamino acids can be obtained by grafting the hydrophobic graft, previously functionalized with the "spacer", directly onto the polymer by a conventional coupling reaction. Block or multiblock polyamino acids PO can be obtained by sequential polymerization of the corresponding amino acid N-carboxy anhydrides (NCA).

For example, a homopolyglutamate or homopolyaspartate polyamino acid or a block, multiblock or random glutamate/aspartate copolymer is prepared by conventional methods.

To obtain a polyamino acid of the alpha type, the most common technique is based on the polymerization of amino acid N-carboxy anhydrides (NCA), which is described e.g. in the article "*Biopolymers*", 1976, 15, 1869, and in the work by H. R. Kricheldorf entitled "*Alpha-amino acid N-carboxy anhydrides and related heterocycles*", Springer Verlag (1987). The NCA derivatives are preferably NCA-O-Me, NCA-O-Et or NCA-O-Bz derivatives (Me=methyl, Et=ethyl and Bz=benzyl). The polymers are then hydrolysed under appropriate conditions to give the polymer in its acid form. These methods are based on the description given in patent FR-A-2 801 226 to the Applicant. A number of polymers that can be used according to the invention, for example of the poly(alpha-L-aspartic), poly(alpha-L-glutamic), poly(alpha-D-glutamic) and poly(gamma-L-glutamic) types of variable molecular weights, are commercially available. The polyaspartic polymer of the alpha-beta type is obtained by the condensation of aspartic acid (to give a polysuccinimide) followed by basic hydrolysis (cf. Tomida et al., Polymer, 1997, 38, 4733-36).

Coupling of the graft with an acid group of the polymer is easily effected by reacting the polyamino acid in the presence of a carbodiimide as coupling agent, and optionally a catalyst such as 4-dimethylaminopyridine, in an appropriate solvent such as dimethylformamide (DMF), N-methylpyrrolidone (NMP) or dimethyl sulfoxide (DMSO). The carbodiimide is e.g. dicyclohexylcarbodiimide or diisopropylcarbodiimide. The grafting rate is controlled chemically by the stoichiometry of the constituents and reactants or by the reaction time. The hydrophobic grafts functionalized with a "spacer" are obtained by conventional peptide coupling or by direct condensation under acid catalysis. These techniques are well known to those skilled in the art.

A block or multiblock copolymer is synthesized using NCA derivatives previously synthesized with the hydrophobic graft. For example, the hydrophobic NCA derivative is copolymerized with NCA-O-benzyl and the benzyl groups are then selectively removed by hydrolysis.

The synthesis of polyamino acids PO preferably produces aqueous suspensions of nanoparticles of PO.

Such suspensions can be converted to powdered nanoparticles of PO by drying in an appropriate manner known to those skilled in the art, for example by heating (oven, etc.), evacuation, use of desiccants, lyophilization or atomization.

These nanoparticles of PO, in suspension or in the pulverulent state, form a starting material for the preparation of the formulations according to the invention.

It may be stated at this point that the formulations according to the invention result from the non-covalent association of nanoparticles based on at least one PO and at least one AP, in an aqueous liquid medium.

For the preparation, the PO and/or the AP can be in solid form (preferably a powder) and/or in liquid form (preferably a colloidal aqueous suspension).

In terms of the present disclosure, AP/PO association means that the AP is (are) associated with the polymer(s) PO [e.g. one or more polyamino acids] by one or more bonds other than a covalent chemical bond or covalent chemical bonds.

The techniques for associating one or more AP with the PO according to the invention are described in particular in patent application WO-A-00/30618. They consist in incorporating at least one AP into the liquid medium containing nanoparticles of PO to give a colloidal suspension of nanoparticles loaded or associated with one or more active principles.

The invention therefore further relates to a process for the preparation of the above-mentioned formulation.

In a first preferred mode of carrying out the invention, this process is characterized in that it consists essentially in:
  taking a colloidal suspension of nanoparticles of at least one PO,
  mixing this colloidal suspension of nanoparticles of PO with at least one AP, preferably in aqueous solution,
  optionally adding at least one excipient,
  adjusting the pH and/or the osmolarity if necessary, and
  optionally filtering the resulting suspension.

Advantageously, the AP is (are) in the form of an aqueous suspension or solution for mixing with the colloidal suspension of nanoparticles of PO.

In a second mode of carrying out the invention, this process is characterized in that it consists essentially in:
  taking a powder of at least one polymer PO,
  mixing this powder with an aqueous suspension or solution of at least one AP, preferably in aqueous solution, optionally adding at least one excipient,
adjusting the pH and/or the osmolarity if necessary, and
optionally filtering the resulting suspension.

The formulations obtained in this way can also be converted to gels, powder or film by the conventional methods known to those skilled in the art, such as concentration by diafiltration or evaporation, coating, atomization or lyophilization, inter alia. These methods can optionally be combined.

Hence there is a third mode of carrying out the process for the preparation of liquid formulations according to the invention, this third mode consisting essentially in:
taking a powder produced by drying the liquid formulation according to the invention as defined above,
mixing this powder with an aqueous liquid medium, preferably with stirring,
optionally adding at least one excipient,
adjusting the pH and/or the osmolarity if necessary, and
optionally filtering the resulting suspension.

Examples of excipients that can be added are antimicrobial agents, buffers, antioxidants and agents for adjusting the isotonicity, which are known to those skilled in the art. Reference may be made e.g. to the work entitled *Injectable Drug Development*, P. K. Gupta et al., Interpharm Press, Denver, Colo., 1999.

If appropriate, the liquid formulation can be sterilized by filtration on filters with a porosity of 0.2 μm, for example. It can then be injected directly into a patient.

All these examples of the preparation of liquid formulations according to the invention are advantageously carried out in the ambient atmosphere and at ambient temperature (e.g. 25° C.).

According to another of its features, the invention encompasses any derived product obtained from the liquid formulation according to the invention as defined above, and comprising submicronic particles formed of PO/AP non-covalent associations as defined above.

In practice, these derived products can consist especially of powders, gels, implants or films, inter alia.

The invention further relates to any precursor of the injectable liquid formulation as defined above.

Still on the subject of these derived products, it must be emphasized that the invention further relates to a process for the preparation of a powder derived from the formulation as defined above, this process being characterized in that said powder is obtained by drying the formulation as defined above.

According to the invention, the AP can be a protein, a glycoprotein, a protein bonded to one or more polyalkylene glycol chains [preferably polyethylene glycol (PEG) chains: "PEGylated protein"], a polysaccharide, a liposaccharide, an oligonucleotide, a polynucleotide or a peptide.

The AP is preferably selected from haemoglobins, cytochromes, albumins, interferons, cytokines, antigens, antibodies, erythropoietin, insulin, growth hormones, factors VIII and IX, interleukins or mixtures thereof, haemopoiesis stimulating factors, and mixtures thereof.

In one variant, the active principle is a "small" hydrophobic, hydrophilic or amphiphilic organic molecule of the type belonging to the anthracycline, taxoid or camptothecin family or of the type belonging to the peptide family, such as leuprolide or cyclosporin, and mixtures thereof.

In terms of the present disclosure, a "small" molecule is especially a small non-protein molecule.

In one valuable variant of the formulation according to the invention which relates to all AP excluding small molecules, the weight fraction of active principle AP not associated with the nanoparticles of polymer PO (expressed in % based on the total weight of the formulation) is such that:
[non-associated AP]$\leq$1,
preferably [non-associated AP]$\leq$0.5.

The primary properties of the formulation according to the invention include its injectability and its ability to form a deposit at the injection site, in vivo, by gelling or by aggregation of the nanoparticles, in the presence of physiological proteins or analogues.

The formulation according to the invention can be injected especially by the parenteral, subcutaneous, intramuscular, intradermal, intraperitoneal or intracerebral route or into a tumour.

The formulation according to the invention can also be administered by the oral, nasal, vaginal, ocular or buccal route.

Advantageously, the formulation is intended for the preparation of drugs, particularly for administration by the parenteral, subcutaneous, intramuscular, intradermal, intraperitoneal or intracerebral route or into a tumour, or by the oral, nasal, vaginal or ocular route.

Although the formulation according to the invention is preferably pharmaceutical, this does not exclude cosmetic, dietetic or phytosanitary formulations comprising at least one PO as defined above and at least one corresponding active principle.

According to yet another of its features, the invention relates to a process for the preparation of drugs, particularly for administration by the parenteral, subcutaneous, intramuscular, intradermal, intraperitoneal or intracerebral route or into a tumour, or by the oral, nasal, vaginal or ocular route, characterized in that it consists essentially in using at least one formulation defined above and/or any derived product and/or any precursor of said formulation.

The invention further relates to a method of therapeutic treatment consisting essentially in administering the formulation as described in the present disclosure by the parenteral, subcutaneous, intramuscular, intradermal, intraperitoneal or intracerebral route or into a tumour, or by the oral, nasal, vaginal or ocular route.

In one particular variant of the invention, this method of therapeutic treatment consists essentially in administering the formulation as described above by injection by the parenteral, subcutaneous, intramuscular, intradermal, intraperitoneal or intracerebral route or into a tumour, preferably in such a way that it forms a gelled/crosslinked deposit at the injection site.

The invention will be understood more clearly and its advantages and variants will become clearly apparent from the Examples below, which describe the synthesis of the PO formed of polyamino acids grafted with a hydrophobic group, and their conversion to a system for the prolonged release of AP, namely a formulation according to the invention (stable aqueous colloidal suspension), and demonstrate the ability of such a system not only to associate with a therapeutic protein, but also, in particular, to gel/crosslink in order to release the therapeutic protein in a very prolonged manner in vivo.

→curve -▲-▲-,
as a function of the time T in hours and at an IFN dose of 60 µg/kg.

Figure 2:
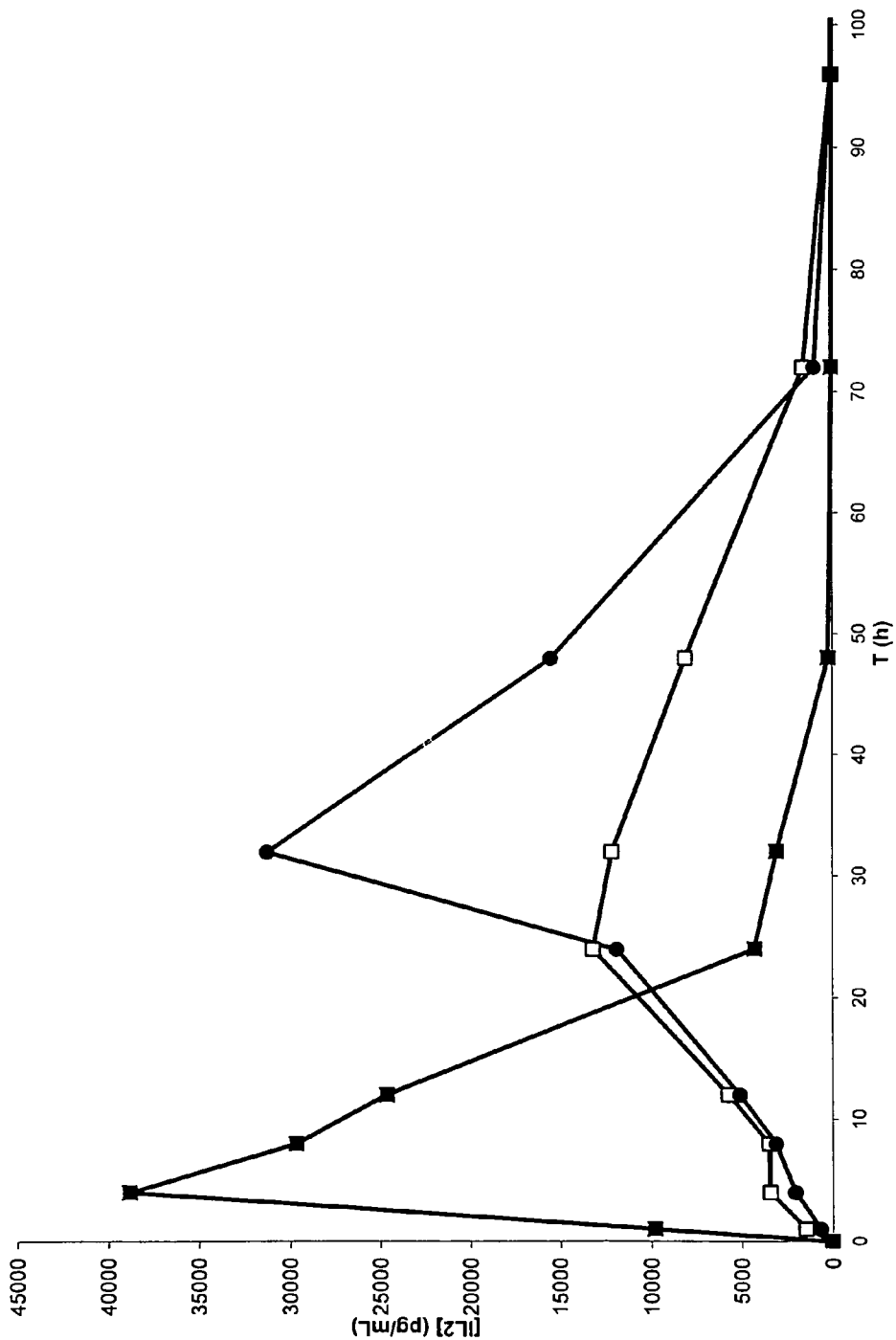

FIG. 2: Curves of the plasma IL2 concentrations (picograms/ml) recorded in the monkey after subcutaneous injection of:
the IL2 formulation according to the invention (Example 11):
→curve -□-□-,
the control IL2 formulation (F) not according to the invention (Example 11):
→curve -✱-z,901 -,
and the control IL2 formulation (G) not according to the invention (Example 11):
→curve -■-■-,
as a function of the time T in hours and at an IL2 dose of 0.5 mg/kg.

EXAMPLES:

Example 1

Amphiphilic Polymer P1

Synthesis of a Polyglutamate Grafted with Alpha-Tocopherol of Synthetic Origin 5.5 g of an alpha-L-polyglutamate (having a molecular weight equivalent to about 10,000 Da, relative to a polyoxyethylene standard, and obtained by the Polymerization of NCAGluOMe followed by hydrolysis, as described in patent application FR-A-2 801 226) are solubilized in 92 ml of dimethylformamide (DMF) by heating at 40° C. for 2 hours. Once the polymer is solubilized, the temperature is allowed to drop to 25° C. and 1.49 g of D,L-alpha-tocopherol (>98%, obtained from Fluka®), previously solubilized in 6 ml of DMF, 0.09 g of 4-dimethylaminopyridine, previously solubilized in 6 ml of DMF, and 0.57 g of diisopropylcarbodiimide, previously solubilized in 6 ml of DMF, are added in succession. After 8 hours at 25° C., with stirring, the reaction medium is poured into 800 ml of water containing 15% of sodium chloride and hydrochloric acid (pH 2). The precipitated polymer is then recovered by filtration and washed with 0.1 N hydrochloric acid and then with water. The polymer is subsequently resolubilized in 75 ml of DMF and then reprecipitated in water containing, as previously, salt and acid to pH 2. After two washes with water, the precipitate is washed several times with diisopropyl ether. The polymer is then dried in an oven under vacuum at 40° C. to give a yield in the order of 85%.

Example 2

Amphiphilic Polymers P2, P3, P4, P5 and P6

These polymers are obtained in the same way as the polymer P1. Table 1 below summarizes the characteristics of these polymers. Those of the polymer P1 are given by way of comparison.

TABLE 1

| Polymer | Mn[1] g/mol of the polyglutamate | Hydrophobic group | % grafting (NMR)[2] | Mn[1] g/mol of the polymer |
|---|---|---|---|---|
| P1 | 10,000 | alpha-tocopherol[3] | 7 | 13,900 |
| P2 | 10,000 | alpha-tocopherol[3] | 4 | 14,400 |
| P3 | 16,900 | alpha-tocopherol[3] | 4 | 15,200 |
| P4 | 10,000 | cholesterol | 5 | 11,500 |
| P5 | 16,900 | cholesterol | 5 | 12,900 |
| P6 | 10,000 | n-dodecanol | 15 | 11,500 |

[1] in polyoxyethylene equivalents
[2] molar grafting rate estimated by proton NMR
[3] of synthetic origin Example 3

Preparation of 30 ml of a Formulation of Interferon Alpha 2b (IFN) Based on the Polymer P6

(a) Preparation of a Colloidal Solution of Amphiphilic Polymer:

1.5 g of lyophilized powder of the amphiphilic polyamino acid P6 of Example 1 above are introduced into a flask. This powder is dissolved in 30 ml of sterile water for injection. The polymer solution is kept at 35° C. for 16 hours, with magnetic stirring. The osmolarity of the solution is adjusted to 275±20 mOsmol with the aid of a Fiske Mark 3 osmometer by introducing the necessary amount of 5.13 M aqueous NaCl solution (30% w/w). The pH is adjusted to 7.4±0.2, if necessary, by the addition of 1 N NaOH solution. The polymer concentration is adjusted to 45 mg/ml by the addition of sterile 0.15 M aqueous NaCl solution. The polymer solution is subsequently filtered on a filter with a pore size of 0.8 and 0.2 micron, and then stored at 4° C.

(b) Association of the Protein with the Polymer:

26.65 ml of the above colloidal solution of polymer P6 and 1.85 ml of IFN solution (PC GEN; concentrated solution containing 2.42 mg/ml) are then mixed in a glass flask. The osmolarity and the pH are readjusted to 300±20 mOsmol and 7.4±0.2, if necessary, by the addition of 0.1 N sodium hydroxide solution and sterile 0.9% sodium chloride. The solution loaded with protein is aged for 5 h at 25° C. in an oven and then filtered on a 0.8-0.2 micron filter. This gives 30 ml of a ready-to-inject formulation containing 0.15 mg/ml of IFN and 40 mg/ml of polymer P6.

Example 4

Preparation of a Long-acting IFN Formulation According to the Present Invention, Based on One of the Polymers P1 to P5

The preparation is carried out as in Example 3, first by preparing a colloidal polymer solution at 1.25 times the desired final concentration and then by mixing this solution with a concentrated interferon solution containing 2.42 mg/ml. The volume of the protein solution is determined by choosing the ratio of the polymer concentration to the intended protein concentration. As in Example 3, the concentration and pH adjustments are made by the addition of NaCl solution and sodium hydroxide solution.

Example 5

Preparation of a Long-Acting Interleukin 2 (IL2) Formulation According to the Present Invention, Based on the Polymer P3

Lyophilized powder of the amphiphilic polymer and sterile water are introduced into a flask in the amount necessary to give a polymer concentration X=1.3 times the desired final concentration in the formulation. Dissolution of the polymer is continued for 16 hours, with magnetic stirring.

The necessary amount of lyophilized IL2 (Prospec) is concentrated to X/(X−1) times the desired final concentration.

The precise concentration of the concentrated IL2 solution is determined by UV assay at 280 nm using a Perkin Elmer Lambda 35 UV spectrophotometer.

This IL2 solution is filtered on a 0.8-0.2 µm filter and stored at 4° C. Its pH is adjusted to 11 by adding 1 M NaOH. The ratio of the protein concentration of this solution to the desired concentration in the formulation is called Y.

The protein solution and the polymer solution are then mixed at ambient temperature. X−1 volumes of protein solution are added per volume of polymer. The pH and the osmolarity are adjusted to 7.4±0.2 and 300±20 mOsm, respectively.

Thus, to prepare a long-acting IL2 formulation according to the invention, based on the polymer P3, containing 20 mg/ml of polymer P3 and 2.5 mg/ml of IL2, the initial polymer solution is concentrated to 26 mg/ml. The initial IL2 solution is concentrated to 11 mg/ml. 0.3 volume of protein solution is added per volume of polymer.

Example 6

Measurement of the Mean Hydrodynamic Diameter of the Nanoparticles of Different Polymers PO According to the Invention The mean hydrodynamic diameter of the particles of polymer PO according to the invention is measured by the Md procedure defined below.

The PO solutions are prepared at concentrations of 1 or 2 mg/ml in 0.15 M NaCl medium and stirred for 24 h. These solutions are then filtered on a 0.8-0.2 µm filter before being analysed by dynamic light scattering using a Brookhaven apparatus operating with a vertically polarized laser beam of wavelength 488 nm. The hydrodynamic diameter of the nanoparticles of polymer PO is calculated from the electric field autocorrelation function by the summation method, as described in the work "Surfactant Science Series" volume 22, Surfactant Solutions, Ed. R. Zana, chap. 3, M. Dekker, 1984.

The following results are obtained for the polymers PO P2, P3, P4 and P6 of Example 2:

TABLE 2

| Polymer | Mean hydrodynamic diameter (nm) |
|---|---|
| P2 | 60 |
| P3 | 90 |
| P4 | 30 |
| P6 | 15 |

Example 7

Spontaneous Association of a Protein with the Nanoparticles of Polymer PO

A 25 mM phosphate buffer solution is prepared from powdered $NaH_2PO_4$ (Sigma ref. S-0751) and adjusted to pH 7.2 with 1 N sodium hydroxide solution (SDS ref. 3470015). A colloidal suspension of nanoparticles of polymer P1 is prepared by dissolving 5 mg/ml of the lyophilized polymer overnight in the above phosphate buffer solution. A stock solution of BSA (Sigma A-2934) is prepared by dissolving 10 mg/ml of the protein for two hours in the same buffer.

The stock solutions and the buffer are filtered on a 0.22 µm filter.

Mixtures are made up by the addition of predetermined volumes of the two stock solutions and dilution in the phosphate buffer, ultimately giving a range of samples having a constant polymer concentration (0.1 mg/ml) and increasing protein concentrations (0 to 1.8 mg/ml).

The samples are left to associate for 5 hours at 25° C., after which they are analysed by capillary electrophoresis using a so-called frontal method, which allows the protein and the protein-polymer complex to be visualized separately. Further details on this technique may be obtained by consulting the following article: Gao J. Y., Dublin P. L., Muhoberac B. B., Anal. Chem., 1997, 69, 2945. The analyses are performed on an Agilent G16000A apparatus equipped with a fused silica bubble capillary (type G1600-62-232). The height of the first plateau, corresponding to the free protein, makes it possible to determine the concentration of non-associated BSA. Experience shows that, for amounts of proteins below 0.1 g of protein per g of polymer, the protein is associated with the nanoparticles of polymer.

Example 8

Determination of the Gelling Concentration C1 for the Polymers PO P1 to P4 and P6

The IG test is applied to formulations of IFN and IL2 associated with the polymers P1 to P6 of Examples 1 and 2. The protein concentrations of these formulations are shown in the Table below. The relaxation time of the formulations in the presence of BSA (concentration 30 mg/ml) is measured by the procedure of the IG test. The critical concentration C1, for which the relaxation time exceeds 1 s, is shown in Tables 3 and 4 for IFN and IL2, respectively.

TABLE

| Induced gelling concentration for IFN formulations | | | | | |
|---|---|---|---|---|---|
| Polymer | P1 | P2 | P3 | P4 | P6 |
| IFN concentration (mg/ml) | 0.3 | 0.15 | 0.15 | 0.15 | 0.3 |
| Concentration C1 (mg/ml) | 17 | >30 | 16 | 17 | >50 |

TABLE 4

| Induced gelling concentration for IL2 formulations | | | |
|---|---|---|---|
| Polymer | P1 | P3 | P6 |
| IL2 concentration (mg/ml) | 2.5 | 2.5 | 2.5 |
| Concentration C1 (mg/ml) | 17 | 17 | >50 |

Example 9

Pharmacokinetics of IFN in the Dog After Subcutaneous Injection of an IFN Formulation Belonging to the Selection According to the Invention A formulation (A) of IFN (concentration 0.3 mg/ml) and amphiphilic polymer P1 (concentration 30 mg/ml) is prepared by the procedure described in Example 3.

This formulation is injected subcutaneously into Beagle dogs (n=3) at a dose of 60 µg/kg. Serum samples are taken at 1, 5, 11, 24, 36, 48, 72, 96, 120, 144, 168 and 240 hours. The plasma IFN concentration is measured on these samples by ELISA (Immunotech IM 3193 kit).

Figure 1:
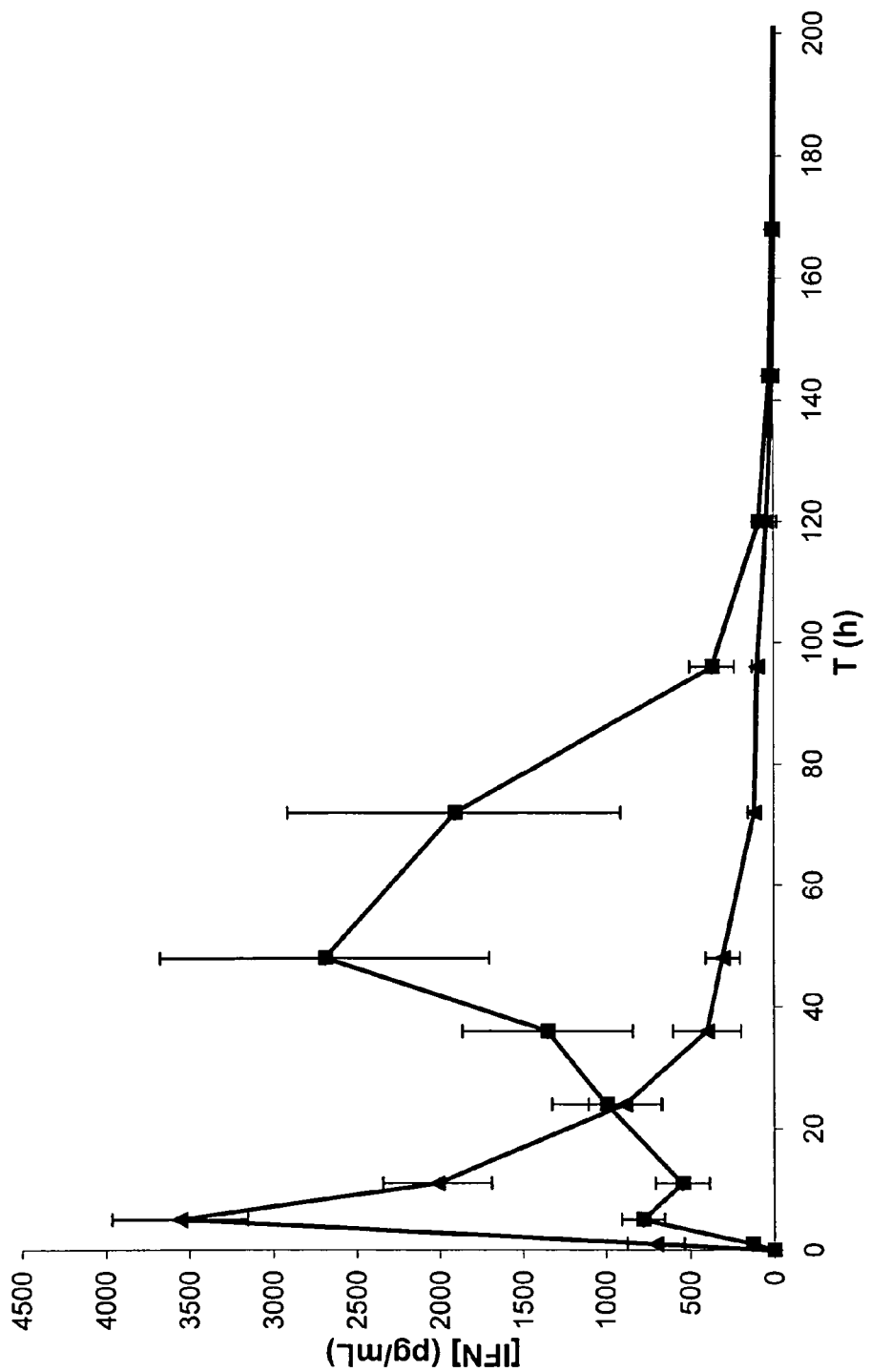
FIG. 1: Curves of the plasma IFN concentrations (picograms/ml) recorded in the dog after subcutaneous injection of:
the IFN formulation (A) according to the invention (Examples 9 & 10):
→curve -■-■-,
and the control IFN formulation (D) not according to the invention (Example 10)

This gives the mean plasma concentration profile shown in FIG. 1, which clearly shows the prolonged release of the protein into the serum compared with a control formulation (D), not according to the invention, of IFN (concentration 0.3 mg/ml) and amphiphilic polymer P6 (concentration 40 mg/ml) (cf. Table 5, Example 10). From a quantitative point of view, the prolongation of the release of IFN by the formulations according to the invention is estimated by measuring:
(a) the time Tmax, which is the median of the time for which the plasma concentration is at a maximum,
(b) the time T50, which is the mean of the time after which the area under the plasma concentration curve reaches 50% of its measured maximum value.

In the case of this formulation, the times Tmax and T50 have the following values:
Tmax=48 hours,
T50=54.2 hours.

Example 10

Pharmacokinetics of IFN in the Dog After Subcutaneous Injection of Various IFN Formulations Based on Amphiphilic Polyamino Acids The following formulations are prepared by the procedure described in Example 3:

TABLE 5

| Formulation | Polymer | Polymer concentration (mg/ml) | IFN concentration (mg/ml) | Relaxation time TR (s) |
|---|---|---|---|---|
| A | P1 | 30 | 0.3 | >10 |
| B | P1 | 10.5 | 0.15 | <0.3 |
| C | P2 | 15 | 0.15 | <0.03 |
| D | P6 | 40 | 0.3 | 0.4 |

The polymer concentration of the formulation A is greater than the gelling concentration C1 measured in Example 8. In other words, the relaxation time measured in the IG test is greater than 1 second. This formulation A therefore belongs to the selection according to the invention. On the other hand, the concentrations of the formulations B, C and D are less than their gelling concentrations, so said formulations do not belong to the selection according to the invention.

These formulations are injected into Beagle dogs at a dose of 60 µg/kg. Plasma samples are taken at 1, 5, 11, 24, 36, 48, 72, 96, 120, 144, 168 and 240 hours. The plasma IFN concentration is measured as in the previous Example.

The times Tmax and T50 for the formulations A, B, C and D are shown in Table 6 below.

TABLE 6

| Reference of formulation | Tmax (h) | T50 (h) |
|---|---|---|
| A | 48 | 54.2 |
| B | 5 | 16.7 |
| C | 11 | 19.3 |
| D | 5 | 17.3 |

Thus the formulation A, which belongs to the selection according to the invention, has a considerably longer release time than the formulations B, C and D, which do not belong to the selection according to the invention.

Example 11

Pharmacokinetics of Interleukin 2 (IL2) in the Monkey After Subcutaneous Injection of Various Formulations Based on Amphiphilic Polyamino Acids The following formulations are prepared by the procedure described in Example 5:

TABLE 7

| Reference | Polymer | Polymer concentration (mg/ml) | IL2 concentration (mg/ml) |
|---|---|---|---|
| E | P1 | 30 | 2.5 |
| F | P3 | 20 | 2.5 |
| G | P6 | 40 | 2.5 |

The formulations E and F, whose polymer concentrations are greater than the gelling concentration C1 measured in Example 8, therefore belong to the selection according to the invention. On the other hand, the concentration of the formulation G is less than the gelling concentration C1, so said formulation does not belong to the selection according to the invention.

These formulations are injected into Cynomolgus monkeys at a dose of 0.5 mg/kg. Plasma samples are taken at 1, 5, 11, 24, 36, 48, 72, 96, 120, 144, 168 and 240 hours. The plasma IL2 concentration is measured on these samples by ELISA (Immunotech IM 3583 kit).

The times Tmax and T50 for the formulations E, F and G are shown in Table 8 below.

TABLE 8

| Reference of formulation | Tmax (h) | T50 (h) |
|---|---|---|
| E | 32 | 34.5 |
| F | 32 | 37.5 |
| G | 4 | 10.5 |

Thus the formulations E and F, which belong to the selection according to the invention, have a considerably longer release time than the formulation G, which does not belong to the selection according to the invention.

Example 12

Observation of the Gelling of the Formulations According to the Invention in Vivo After Subcutaneous Injection The subcutaneous behaviour of the formulations according to the invention was studied in the domestic pig. Six domestic pigs were injected under the abdominal skin, to a depth of 4 mm, with 0.3 ml of the following formulations:
Formulation A: isotonic aqueous solution, pH 7.3, of the polymer P6 of Example 2 at a concentration of 45 mg/ml.
Formulation B: isotonic aqueous solution, pH 7.3, of the polymer P1 of Example 1 at a concentration of 20 mg/ml.

Samples were taken from the injected sites 72 hours after administration. Histological examination discloses the presence of a gelled deposit of polymer for the formulation B. It takes the form of uniformly coloured plaques. By contrast, this phenomenon is not observed for the formulation A, for which the polymer has infiltrated between the collagen fibres.

It may be emphasized that the polymer matrix B is perfectly biodegradable since the tissue has completely returned to its normal state after 21 days.

The invention claimed is:

1. A liquid pharmaceutical formulation for the prolonged release of active principle(s) (AP), wherein:

said formulation is liquid under injection conditions;

said formulation is liquid at physiological temperature and at physiological pH and in the presence of:
  a physiological electrolyte in a physiological concentration, or
  at least one surfactant, said formulation comprises an aqueous colloidal suspension of low viscosity based on submicronic particles of water-soluble biodegradable polymer [PO] non-covalently associated with at least one active principle (AP);

wherein said [PO] is a polyamino acid formed of aspartic residues, glutamic residues, or both aspartic and glutamic residues, at least one of said residues carrying at least one tocopherol group attached laterally to the chain, and wherein the concentration of [PO] is greater than or equal to 0.9×C1, where C1 is the "induced gelling" concentration of the particles of [PO], as measured in an induced gelling (IG) test, said test comprising the following steps:

dissolving increasing amounts of amphiphilic polymer [PO] in a dry powdered form in deionized water, and keeping the obtained solutions at 25° C. for 16 hours, with magnetic stirring, mixing said solutions with a concentrated solution of active principle(s) to get the desired active principle(s) concentration(s)

mixing said solutions with a concentrated aqueous solution of bovine serum albumin (BSA) to obtain a solution containing 30 mg/ml of BSA, and centrifuging for 15 minutes at 3000 rpm, stirring gently for 24 h, measuring the relaxation time Tr of the polymer [PO] solutions to define the concentration C1 at which this time Tr exceeds 1 second; and said formulation prolongs and controls the in vivo release time of the AP beyond 24 h after administration.

2. The formulation according to claim 1, wherein the concentration of [PO] is: $20 \times C1 \geqq [PO] \geqq C1$.

3. The formulation according to claim 1 wherein said formulation has a viscosity less than or equal to 5 Pa·s.

4. The formulation according to claim 1, the [PO] is defined by general formula (I) below:

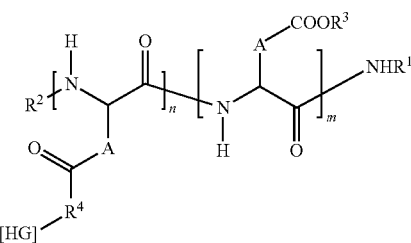

in which:

$R^1$ is selected from the group consisting of: H, a linear C2 to C10 alkyl or branched C3 to C10 alkyl, benzyl, a terminal amino acid residue, and —$R^4$-[HG];

$R^2$ is selected from the group consisting of: H, a linear C2 to C10 acyl or branched C3 to C10 acyl group, a pyroglutamate and —$R^4$-[HG];

$R^3$ is selected from the group consisting of: H and a cationic entity selected from the group consisting of:

metal cations selected from the subgroup consisting of sodium, potassium, calcium and magnesium, organic cations selected from the subgroup consisting of:

cations based on amine, cations based on oligoamine, cations based on polyamine, and cations based on amino acid(s) selected from the class consisting of:

cations based on lysine or arginine, and cationic polyamino acids selected from the subgroup comprising polylysine and oligolysine;

$R^4$ is a direct bond or a spacer based on 1 to 4 amino acid residues;

A independently is a radical —$CH_2$— or —$CH_2$—$CH_2$—;

n/(n+m) is defined as the molar grafting rate;

n/(n+m) is between 1 and 25 mol%;

n+m varies from 10 to 1000; and

[HG] is a tocopherol.

5. The formulation according to claim 1, the [PO] has one of general formulae (II), (III) and (IV) below:

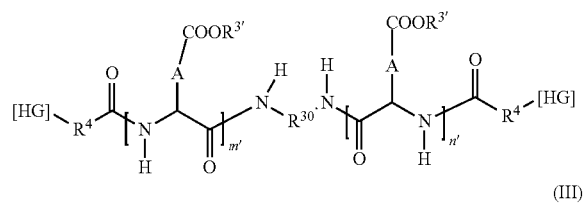

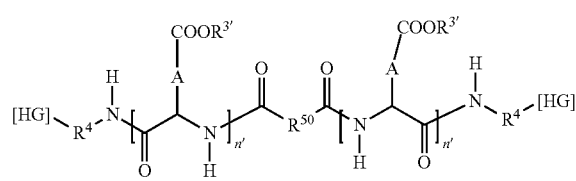

-continued

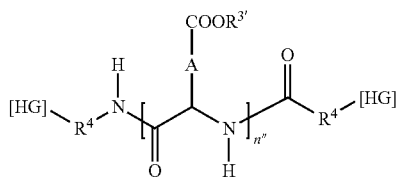

(IV)

in which:
[HG] is a tocopherol;
$R^{30}$ is a linear C2 to C6 alkyl group;
$R^{3'}$ is H or a cationic entity selected from the group comprising:
  metal cations selected from the subgroup consisting of sodium, potassium, calcium and magnesium,
  organic cations selected from the subgroup consisting of: cations based on amine, cations based on oligoamine, cations based on polyamine, and cations based on amino acid(s) selected from the class comprising cations based on lysine or arginine, and cationic polyamino acids selected from the subgroup comprising polylysine and oligolysine;
$R^{50}$ is a C2 to C6 alkyl, dialkoxy or diamine group;
$R^4$ is a direct bond or a "spacer" based on 1 to 4 amino acid residues;
A independently is a radical —$CH_2$— or —$CH_2$—$CH_2$—;
n'+m' or n" is defined as the degree of polymerization and varies from 10 to 1000.

6. The formulation according to claim 1, the [PO] comprises an alpha-L-glutamate or alpha-L-glutamic homopolymer.

7. The formulation according to claim 1, wherein the [PO] comprises an alpha-L-aspartate or alpha-L-aspartic homopolymer.

8. The formulation according to claim 1, wherein the [PO] comprises an alpha-L-aspartate/alpha-L-glutamate or alpha-L-aspartic/alpha-L-glutamic copolymer.

9. The formulation according to claim 8, wherein, in the [PO], the distribution of the aspartic and glutamic residues carrying grafts containing at least one tocopherol is either random or of the block type or of the multiblock type.

10. The formulation according to claim 1, wherein the molecular weight of the [PO] is between 2,000 and 100,000 g/mol.

11. The formulation according to claim 1, wherein the [PO] further carries at least one graft of polyalkylene glycol type bonded to a glutamate or an aspartate residue.

12. The formulation according to claim 11, wherein the graft of polyalkylene glycol type has formula (V) below:

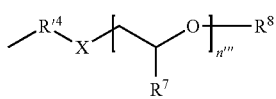

(V)

in which:

$R'^4$ is a direct bond or a "spacer" based on 1 to 4 amino acid residues;
X is a heteroatom selected from the group consisting of: oxygen, nitrogen and sulfur;
$R^7$ and $R^8$ independently are H or a linear C1 to C4 alkyl;
n'" varies from 10 to 1000.

13. The formulation according to claim 11, wherein the polyalkylene glycol is a polyethylene glycol.

14. The formulation according to claim 11, wherein the molar percentage of polyalkylene glycol grafting varies from 1 to 30%.

15. The formulation according to claim 1, wherein the AP is selected from the group consisting of: a protein, a glycoprotein, a protein bonded to one or more polyalkylene glycol chains, a polysaccharide, a liposaccharide, an oligonucleotide, a polynucleotide and a peptide.

16. The formulation according to claim 1, wherein the AP is a "small" hydrophobic, hydrophilic or amphiphilic organic molecule.

17. The formulation according to claim 1, wherein the weight fraction of AP not associated with the submicronic particles [non-associated AP], in weight %, is [non-associated AP]≦1.

18. The formulation according to claim 1 wherein the formulation is for administration by the parenteral, subcutaneous, intramuscular, intradermal, intraperitonial or intracerebral route or into a tumor, or by the oral, nasal, vaginal or ocular route.

19. A process for the preparation of the formulation of claim 1, said process comprising the steps of:
  taking a colloidal suspension of nanoparticles of at least one PO,
  mixing this colloidal suspension of nanoparticles of PO with at least one AP, in aqueous solution, and
  adjusting the pH and/or the osmolarity if necessary.

20. A process according to claim 19, wherein the at least one AP is in the form of an aqueous suspension or solution for mixing with the colloidal suspension of nanoparticles of PO.

21. A process for the preparation of the formulation of claim 1, said process comprising the steps of:
  taking a powder of nanoparticles of at least one PO,
  mixing this powder with an aqueous suspension or solution of at least one AP, in aqueous solution, and
  adjusting the pH and/or the osmolarity if necessary.

22. A process for the preparation of the formulation of claim 1, said process comprising the steps of:
  taking a powder produced by drying the liquid formulation according to claim 1, mixing this powder with an aqueous liquid medium, and adjusting the pH and/or the osmolarity if necessary.

23. The formulation according to claim 1, wherein the concentration of [PO] is: 10×C1≧[PO]≧C1.

24. The formulation according to claim 1, wherein the molecular weight of the [PO] is between 5,000 and 40,000 g/mol.

* * * * *